(12) United States Patent
Bruce et al.

(10) Patent No.: US 12,390,219 B2
(45) Date of Patent: Aug. 19, 2025

(54) SURGICAL STAPLER WITH CLAMP FORCE SENSOR

(71) Applicant: Cilag GmbH International, Zug (CH)

(72) Inventors: John K. Bruce, Morrow, OH (US); Devanathan Raghavan, Mason, OH (US); Chad P. Boudreaux, Cincinnati, OH (US); Bradley A. Arnold, Mason, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 18/502,500

(22) Filed: Nov. 6, 2023

(65) Prior Publication Data
US 2025/0143697 A1    May 8, 2025

(51) Int. Cl.
*A61B 17/072* (2006.01)
*A61B 17/00* (2006.01)
*A61B 90/00* (2016.01)

(52) U.S. Cl.
CPC .. *A61B 17/072* (2013.01); *A61B 2017/00022* (2013.01); *A61B 2017/00119* (2013.01); *A61B 2017/00221* (2013.01); *A61B 2017/00734* (2013.01); *A61B 2017/07257* (2013.01); *A61B 2017/07271* (2013.01); *A61B 2090/064* (2016.02); *A61B 2562/0261* (2013.01)

(58) Field of Classification Search
CPC ........ A61B 17/072; A61B 2017/00022; A61B 2017/00119; A61B 2017/00221; A61B 2017/00734; A61B 2017/07257; A61B 2017/07271; A61B 2090/064; A61B 2562/0261
See application file for complete search history.

(56) References Cited

U.S. PATENT DOCUMENTS

| | | |
|---|---|---|
| 6,988,650 B2 | 1/2006 | Schwemberger et al. |
| 7,134,587 B2 | 11/2006 | Schwemberger et al. |
| 7,147,139 B2 | 12/2006 | Schwemberger et al. |
| 7,204,404 B2 | 4/2007 | Nguyen et al. |
| 7,207,472 B2 | 4/2007 | Wukusick et al. |
| 10,045,780 B2 | 8/2018 | Adams et al. |
| 10,194,913 B2 | 2/2019 | Nalagatla et al. |
| 2005/0139636 A1 | 6/2005 | Schwemberger et al. |
| 2005/0143759 A1 | 6/2005 | Kelly |
| 2005/0145672 A1 | 7/2005 | Schwemberger et al. |
| 2012/0193396 A1* | 8/2012 | Zemlok ............ A61B 17/07207 227/176.1 |

(Continued)

*Primary Examiner* — Anna K Kinsaul
*Assistant Examiner* — Himchan Song
(74) *Attorney, Agent, or Firm* — Frost Brown Todd LLP

(57) ABSTRACT

A surgical instrument includes a handle assembly, a shaft assembly, an end effector and a clamp force sensor. The handle assembly includes a closure trigger that is pivotable between a released position and an actuated position. The end effector is coupled with the shaft assembly and includes a cartridge that includes an anvil and a cartridge housing. The cartridge housing is slidable with respect to the anvil between an unclamped position and a clamped position to facilitate selective clamping of patient tissue therebetween. The clamp force sensor is associated with the end effector and is configured to detect a clamping force between the anvil and the cartridge housing and facilitate generation of a notification as a function of the detected clamping force.

20 Claims, 32 Drawing Sheets

(56) References Cited

U.S. PATENT DOCUMENTS

| | | | | |
|---|---|---|---|---|
| 2012/0228358 A1* | 9/2012 | Zemlok | ................ | A61B 17/072 |
| | | | | 227/176.1 |
| 2014/0110456 A1* | 4/2014 | Taylor | .................... | A61B 90/90 |
| | | | | 227/176.1 |
| 2015/0060518 A1* | 3/2015 | Shelton, IV | ........... | A61B 34/30 |
| | | | | 227/175.2 |
| 2018/0256161 A1* | 9/2018 | Eschbach | .............. | A61B 17/068 |
| 2019/0200981 A1* | 7/2019 | Harris | .................... | H04N 7/183 |
| 2021/0386424 A1* | 12/2021 | Abramek | ......... | A61B 17/07207 |
| 2022/0218337 A1* | 7/2022 | Timm | ............ | A61B 17/320068 |
| 2022/0346781 A1* | 11/2022 | Shelton, IV | ....... | A61B 17/0686 |
| 2023/0007859 A1 | 1/2023 | Adams et al. | | |
| 2023/0098870 A1* | 3/2023 | Harris | ................... | G16H 40/67 |
| | | | | 606/41 |

\* cited by examiner

SURGICAL STAPLER WITH CLAMP FORCE SENSOR

BACKGROUND

Some surgical staplers are operable to clamp down on one or more layers of patient tissue, form staples through the layers of tissue to substantially seal the layers of tissue together near the formed staples and cut through the layers of tissue for forming severed ends of operatively sealed tissue. An illustrative stapling instrument may include a pair of cooperating elongate jaw members, where each jaw member may be adapted to be inserted into a patient and positioned relative to tissue that is to be stapled and/or incised. One of the jaw members may support a staple cartridge with at least two laterally spaced rows of staples contained therein, and the other jaw member may support an anvil with staple-forming pockets aligned with the rows of staples in the staple cartridge. Generally, the stapling instrument may further include a pusher bar and a knife blade that are slidable relative to the jaw members to sequentially or simultaneously eject the staples from the staple cartridge via camming surfaces on the pusher bar and/or camming surfaces on a wedge sled that is pushed by the pusher bar. The camming surfaces may be configured to activate one or more staple drivers carried by the cartridge and associated with the staples in order to push the staples against the anvil and form laterally spaced rows of deformed staples in the tissue gripped between the jaw members. Such rows may be arranged as linear rows and/or arcuate rows for sequentially or simultaneously stapling and cutting the tissue of the patient in the form of a predetermined pattern. The knife blade may trail the camming surfaces and cut the tissue along a linear or arcuate line between the rows of staples formed in the tissue.

Merely illustrative surgical staplers are disclosed in U.S. Pat. No. 6,988,650, entitled "Retaining Pin Lever Advancement Mechanism for a Curved Cutter Stapler," issued Jan. 24, 2006; U.S. Pat. No. 7,134,587, entitled "Knife Retraction Arm for a Curved Cutter Stapler," issued Nov. 14, 2006; U.S. Pat. No. 7,147,139, entitled "Closure Plate Lockout for a Curved Cutter Stapler," issued Dec. 12, 2006; U.S. Pat. No. 7,147,140, entitled "Cartridge Retainer for a Curved Cutter Stapler," issued Dec. 12, 2006; U.S. Pat. No. 7,204,404, entitled "Slotted Pins Guiding Knife in a Curved Cutter Stapler," issued Apr. 17, 2007; and U.S. Pat. No. 7,207,472, entitled "Cartridge with Locking Knife for a Curved Cutter Stapler," issued Apr. 24, 2007. The disclosure of each of the above-cited U.S. Patents is incorporated by reference herein. Additional merely illustrative surgical staplers are disclosed in U.S. Pat. Pub. No. 2005/0139636, entitled "Replaceable Cartridge Module for a Surgical Stapling and Cutting Instrument," published on Jun. 30, 2005, now abandoned; U.S. Pat. Pub. No. 2005/0143759, entitled "Curved Cutter Stapler Shaped for Male Pelvis," published on Jun. 30, 2005, now abandoned; and U.S. Pat. Pub. No. 2005/0145672, entitled "Curved Cutter Stapler with Aligned Tissue Retention Feature," published on Jul. 7, 2005, now abandoned. The disclosure of each of the above-cited U.S. Patent Publications is incorporated by reference herein.

A surgical stapler may be inserted into a patient to perform colorectal surgery. Such procedures may include the use of the stapler to operatively seal, sever, and remove the colon of the patient, in whole or in part. For instance, a proctocolectomy may be performed during a lower anterior resection ("LAR") for treating and inhibiting the spread of colorectal cancer cells. Of course, surgical staplers may be used in various other settings and procedures.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1A:
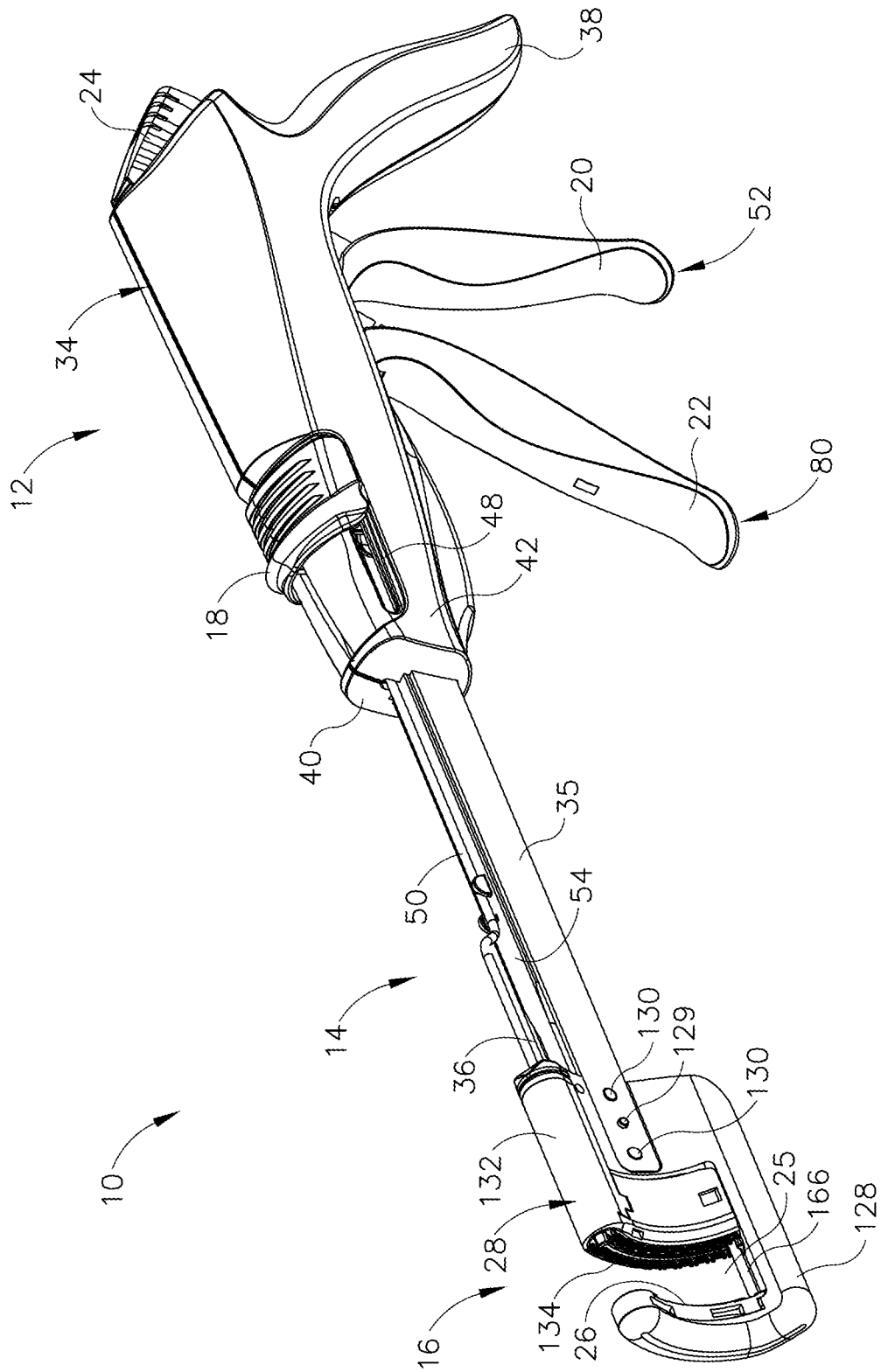
FIG. 1A depicts a right front perspective view of an illustrative surgical stapling instrument with a pin actuation mechanism in an open position and a staple cartridge in open position.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. It will be further appreciated that for convenience and clarity, spatial terms such as "vertical," "horizontal," "lower," "upper," "front," and "rear" are used herein with respect to the drawings. However, surgical instruments are used in many orientations and positions, and these terms are not intended to be limiting and/or absolute.

I. Illustrative Surgical Stapler

FIG. 1A depicts an illustrative surgical stapling and severing instrument (10) that includes a handle assembly (12), a shaft assembly (14), and an end effector (16) distally projecting from shaft assembly (14). It should be understood that terms such as "proximal," "distal," "right," and "left"

are used herein with reference to a clinician gripping handle assembly (12) of surgical stapling instrument (10). Thus, end effector (16) is distal with respect to the relatively proximal handle assembly (14).

Except as otherwise described herein, instrument (10) may be configured and operable in accordance with at least some of the teachings of U.S. Pat. Pub. No. 2005/0143759, entitled "Curved Cutter Stapler Shaped for Male Pelvis," published on Jun. 30, 2005, now abandoned, the disclosure of which is incorporated by reference herein; U.S. Pat. No. 10,045,780, entitled "Method of Applying Staples in Lower Anterior Bowel Resection," issued Aug. 14, 2018, the disclosure of which is incorporated by reference herein; U.S. Pat. No. 10,194,913, entitled "Surgical Instrument Comprising Systems for Assuring the Proper Sequential Operation of the Surgical Instrument," issued Feb. 5, 2019, the disclosure of which is incorporated by reference herein; and/or U.S. Pat. Pub. No. 2023/0007859, entitled "Cartridge Retention Features for Curved Surgical Stapler," published Jan. 12, 2023.

Figure 1B:
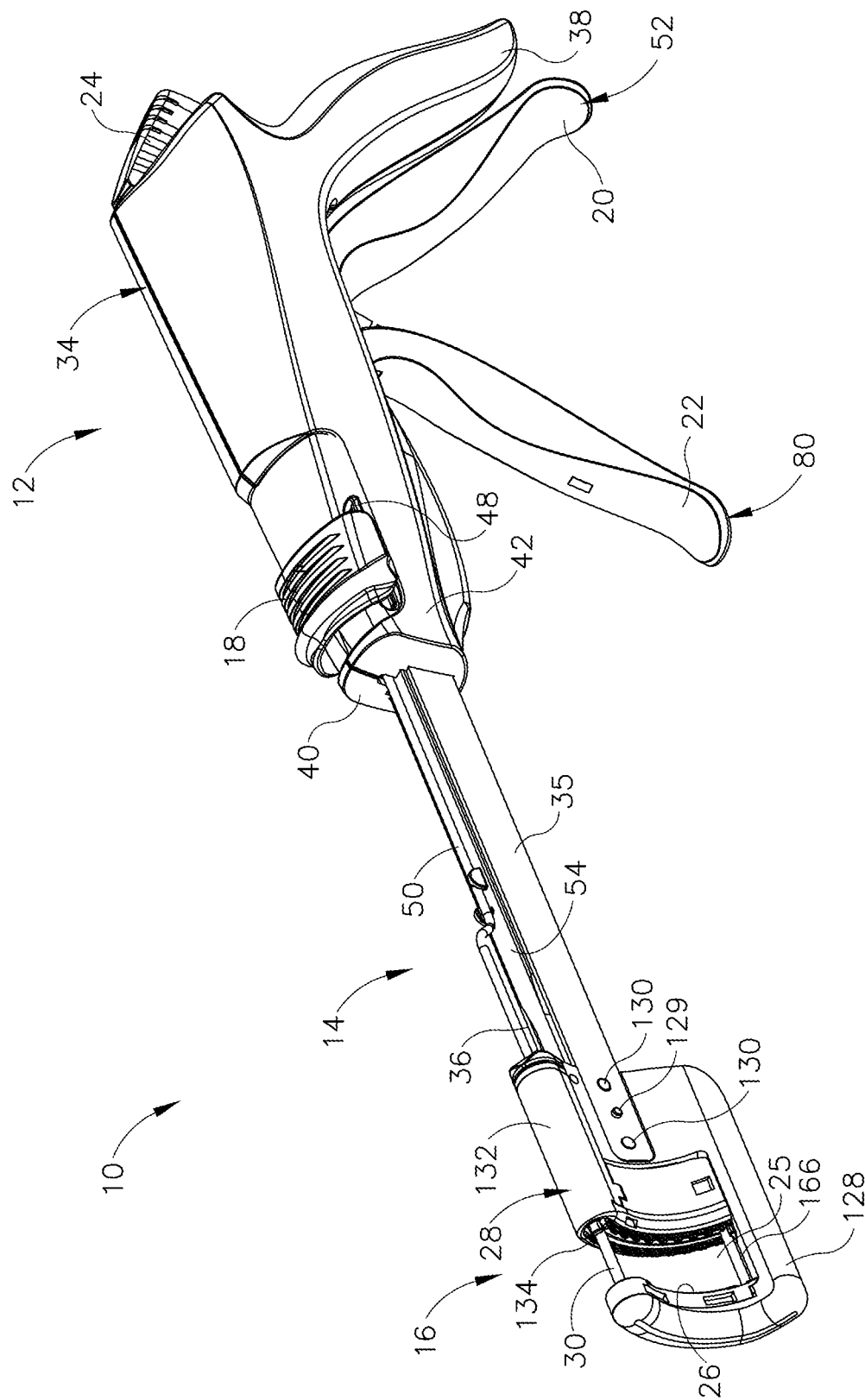
FIG. 1B depicts a right front perspective view of the surgical stapling instrument of FIG. 1A with the pin actuation mechanism in a closed position and the staple cartridge in the open position.

Handle assembly (12) includes several actuation mechanisms for operating end effector (16) during the surgical procedure. To this end, illustrative handle assembly (12) includes a saddle shaped slide (18), a closure trigger (20), and a firing trigger (22) in communication with end effector (16) via shaft assembly (14). As shown in FIG. 1A, slide (18) and closure trigger (20) are in open configurations such that end effector (16) is configured to receive tissue laterally within a gap (25) between an anvil (26) and a cartridge (28) of end effector (16). Translating slide (18) distally toward end effector (16) slides a retaining pin (30) of end effector distally as shown in FIG. 1B for capturing the tissue between anvil (26) and cartridge (28). With respect to FIGS. 1C and 1D, sequentially actuating closure trigger (20) and firing trigger (22) respectively compresses the tissue between anvil (26) and cartridge (28) in a closed configuration and then forms a plurality of staples (not shown) within the tissue and severs the tissue with a knife (32) (see FIG. 6) for treatment. Additional details regarding these illustrative actuation mechanisms will be provided below in greater detail.

A. Illustrative Handle Assembly and Shaft Assembly

Figure 2A:
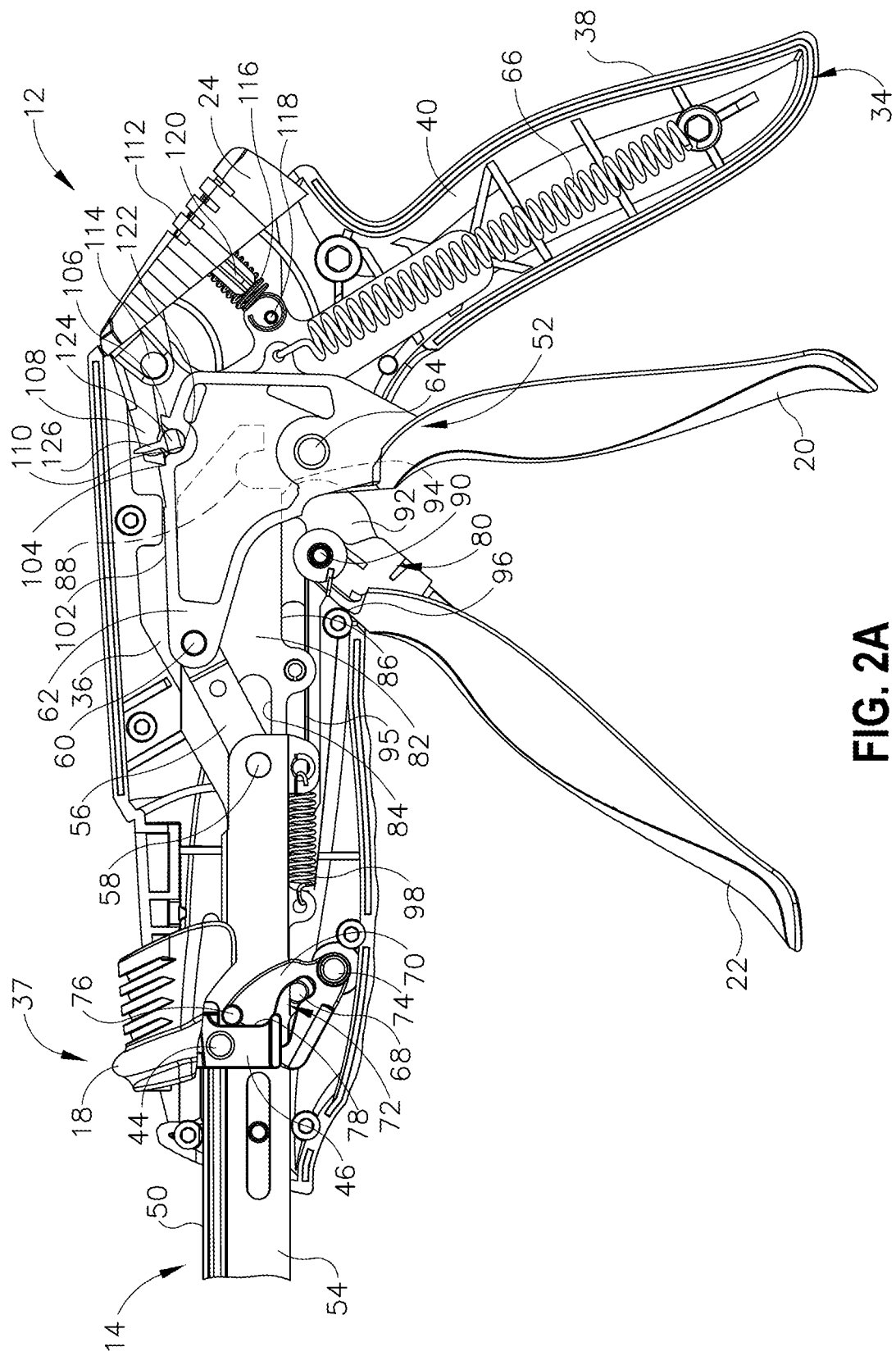
FIG. 2A depicts a right side elevational view of a handle assembly of the surgical stapling instrument of FIG. 1A, with various components removed for clarity, and with the pin actuation mechanism in the closed position and the staple cartridge in the open position.

As shown in FIGS. 1A and 2A, handle assembly (12) has a handle housing (34), a pair of handle frame plates (35, 36) within handle housing (34) extending along shaft assembly (14), saddle shaped slide (18), closure trigger (20), and firing trigger (22) as briefly discussed above. Handle housing (34) defines a hand grip (38), which the operator, such as a surgeon, grasps with the palm of at least one hand. Handle housing (34) is formed by a right shroud handle portion (40) and a left shroud handle portion (42). Closure trigger (20) is proximally positioned relative to firing trigger (22) and each are pivotally mounted to frame plates (35, 36) to extend underneath a remainder of handle assembly (12) for manipulation by the fingers of the operator. Closure and firing triggers (20, 22) are shown in unactuated positions prior to closing end effector (16) and firing staples (not shown) and/or knife (32) (see FIG. 6). Consequently, cartridge (28) is spaced from anvil (26) for receiving tissue within gap (25) therebetween.

Surgical stapling instrument (10) captures tissue via a tissue retaining pin actuation mechanism (37) prior to actuation of the closure and firing triggers (20, 22). FIG. 1A shows retaining pin actuation mechanism (37), which includes slide (18), in the open configuration, whereas FIG. 2A shows retaining pin actuation mechanism (37) in the closed configuration in greater detail. With respect to FIG. 2A, slide (18) is mounted on an upper surface of handle housing (34) and is configured to linearly translate between proximal and distal positions. Slide (18) connects to posts (44), which extend laterally outwardly from a push rod driver (46), through slots (48) (see FIG. 1A). Push rod driver (46) is restrained within handle housing (34) along longitudinal movement by slots (48). Push rod driver (46) is connected to a proximal end of a push rod (50). A distal end of push rod (50) connects to retaining pin (30) (see FIG. 6) such that distal movement of slide (18) causes push rod (50) to similarly slide proximally along shaft assembly (14) for moving retaining pin (30) (see FIG. 6) to the closed configuration, which will be discussed below in greater detail.

A closure mechanism (52), which includes closure trigger (20), is configured to selectively move cartridge (28) toward the tissue positioned between anvil (26) and cartridge (28) in the closed configuration in anticipation of stapling and/or cutting the tissue. Closure mechanism (52) further includes an elongated closure member (54), with a generally U-shaped cross-section, extending distally from handle assembly (12), through shaft assembly (14), and into end effector (16) for receiving a cartridge (28) (see FIG. 3) at a distal end portion thereof as discussed below. A proximal end portion of closure member (54) is operatively connected to closure trigger (20) by a plurality of linkages configured to convert pivoting motion of closure trigger (20) into translation of closure member (54). More particularly, the intermediate and proximal end portions of closure member (54) extend through handle assembly (12) between left and right handle frame plates (35, 36). Right and left closure links (56) are respectively pivotally attached at the right and left proximal ends of closure member (54) by an integral closure link pin (58). At an opposite end of the closure links (56), closure links (56) are pivotally attached to another integral closure link pin (60). Closure link pin (60) connects closure links (56) to a slotted closure arm link (62), which is pivotally mounted to handle frame plates (35, 36) at a closure trigger pin (64). Closure trigger (20) descends from the slotted closure arm link (62) for pivotal rotation about closure trigger pivot pin (64) both toward and away from hand grip (38). A closure spring (66) housed within hand grip (38) is secured to the slotted closure arm link (62) to provide a desired resistance when the operator squeezes closure trigger (20) toward hand grip (38), and to bias closure trigger (20) toward the open position.

Closure member (54) is further configured for directing movement of tissue retaining pin actuation mechanism (37) to automatically direct movement of the retaining pin (30) to the closed configuration while the operator squeezes closure trigger (20). Such automation may be useful in the event that the operator did not manually move the slide (18) to the distal position before actuating trigger (20). Closure member (54) includes posts (68), which extend laterally on each opposing side of closure member (54) within handle housing (34). Posts (68) slidably connect to a yoke (70) via L-shaped slots (72). Yoke (70) is pivotally mounted within handle housing (34) by a pivot pin (74). Yoke (70) further includes cam pins (76) that are configured to push camming surfaces (78) on push rod driver (46). Thus, actuating closure trigger (20) to an intermediate position shown in FIG. 2A directs the closure member (52) distally and, in turn, causes yoke (70) to engage push rod driver (46) and force retaining pin (30) (see FIG. 1B) to the closed position. Slide (18) is thereby dragged along handle housing (34) from the proximal position to the distal position in the event that the operator did not manually manipulate slide (18) to the distal position before actuating trigger (20).

Figure 1C:
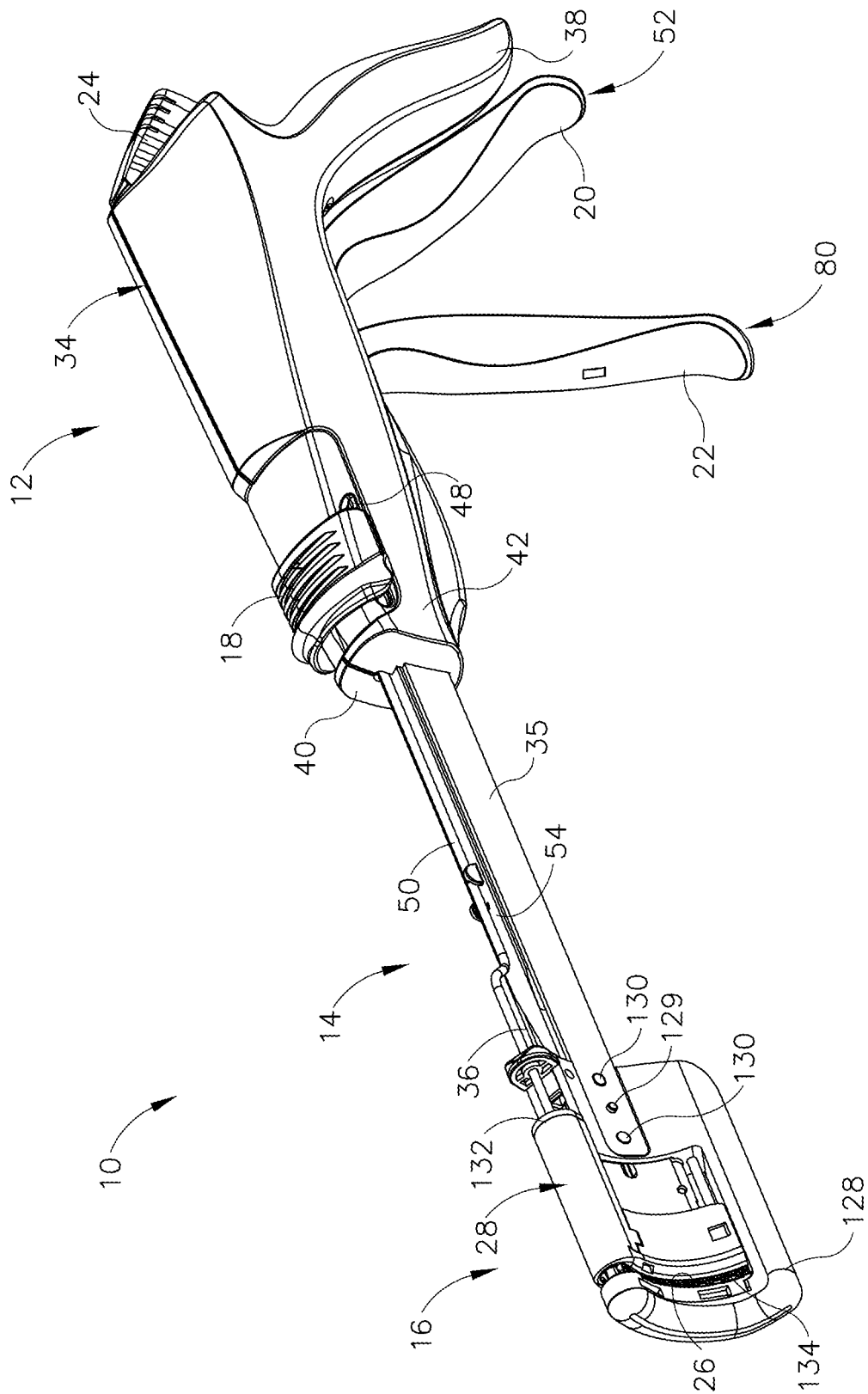
FIG. 1C depicts a right front perspective view of the surgical stapling instrument of FIG. 1A with the pin actuation mechanism in the closed position and the staple cartridge in a closed position via actuation of a closure mechanism.
Figure 1D:
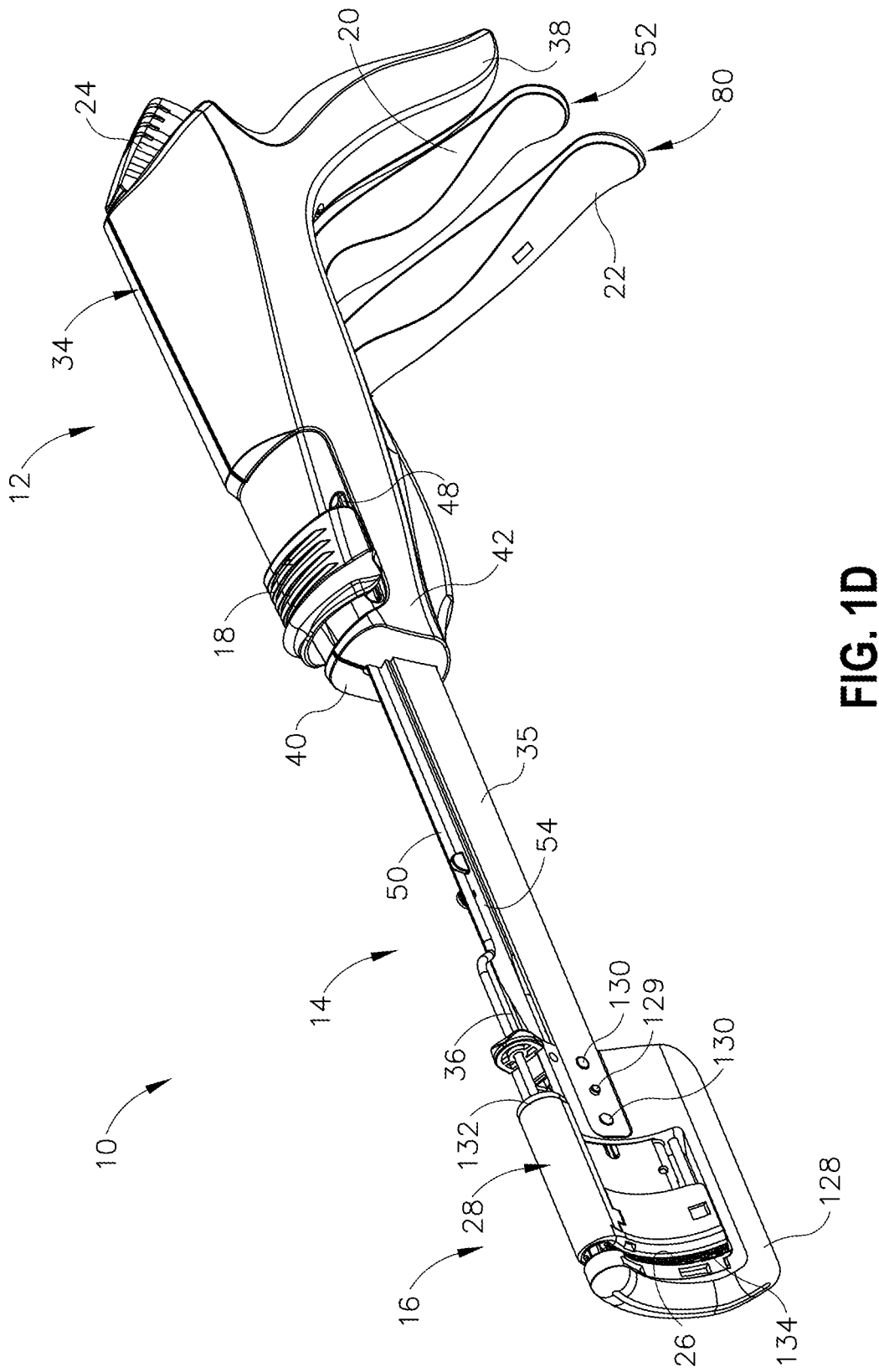
FIG. 1D depicts a right front perspective view of the surgical stapling instrument of FIG. 1A with the pin actuation mechanism and the staple cartridge in the closed positions and a firing trigger in a fired position for stapling and cutting tissue of a patient.
Figure 2B:
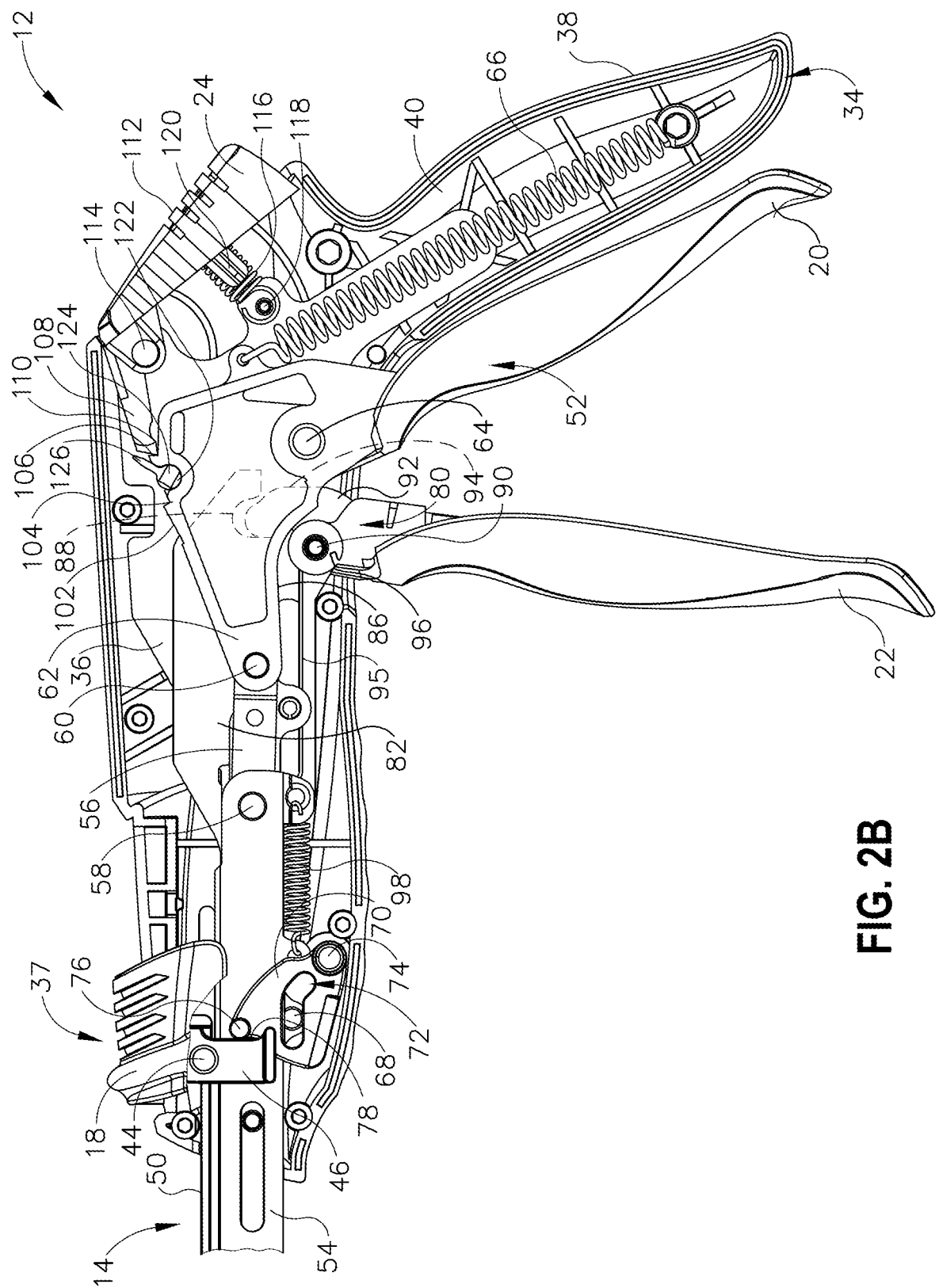
FIG. 2B depicts a right side elevational view of the handle assembly of the surgical stapling instrument of FIG. 1A, with various components removed for clarity, and with the pin actuation mechanism in the closed position and the staple cartridge in the closed position via actuation of the closure mechanism.
Figure 2C:
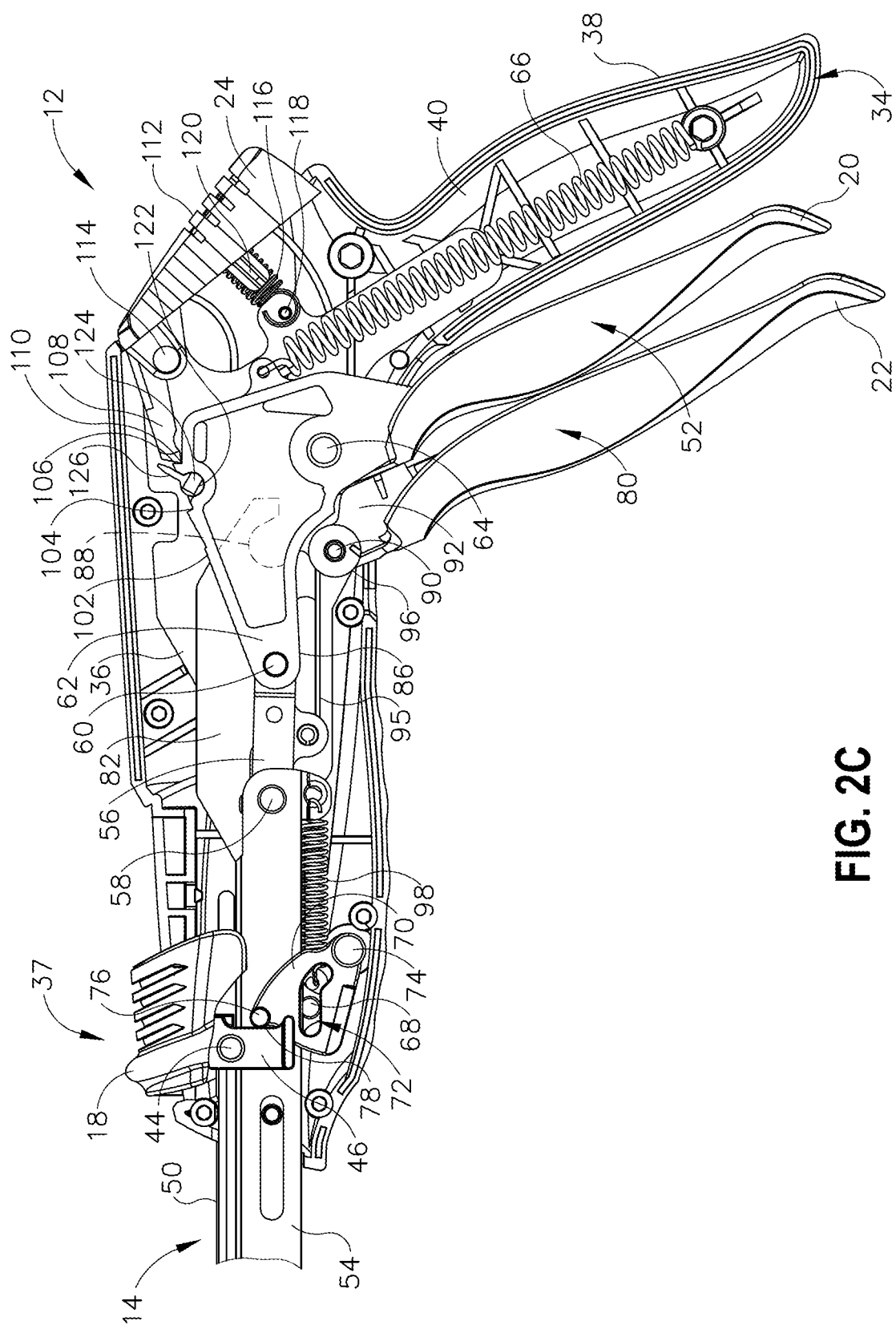
FIG. 2C depicts a right side elevational view of the handle assembly of the surgical stapling instrument of FIG. 1A, with various components removed for clarity, and with the pin actuation mechanism and the staple cartridge in the closed positions and the firing trigger in the fired position for stapling and cutting tissue of a patient.

The operator further squeezes the closure trigger (20) to the hand grip (38) as shown in FIGS. 1C and 2B to effectively set surgical stapling instrument (10) in the closed configuration prior to forming the staples (not shown) and severing the tissue as discussed briefly above. Illustrative handle assembly (12) is configured to form the staples (not shown) and sever the tissue via a firing mechanism (80) upon operator manipulation of firing trigger (22) toward closure trigger (20) as shown in FIGS. 1D and 2C. With respect to FIGS. 1C, 1D, 2B, and 2C, firing mechanism (80), which includes firing trigger (22), has a firing bar (82) extending distally from handle assembly (12) and within end effector (16). A distal end of firing bar (82) cooperates with cartridge (28) as discussed below in greater detail, whereas a proximal end of firing bar (82) is operatively connected to firing trigger (80) for selective firing thereof.

Firing bar (82) has a rectangular receiving slot (84) (see FIG. 2A) in a portion of firing bar (82) positioned within handle housing (34). Integral closure link pin (58) extends through receiving slot (84). The underside of the proximal end portion of firing bar (82) has a sliding surface (86). The proximal end portion of firing bar (82) also has a terminal side engagement surface (82) extending from sliding surface (86). Firing trigger (22) is pivotally mounted to handle frame plates (35, 36) by a firing trigger pin (90) spaced from closure trigger pin (64) such that each of pins (90, 64) pivot about mutually independent axes. Firing trigger (22) includes an arcuate firing trigger link (92) extending from firing trigger (22) at firing trigger pin (90) to an apex (94), which rests on sliding surface (86) of the proximal end portion of firing bar (82). Within handle assembly (12), firing trigger (22) is attached to firing trigger spring arms (95, 96), respectively. Firing trigger spring arms (95, 96) support a torsion spring (not shown) on the right half of firing trigger (22). Finally, a firing bar return spring (98) is secured to the underside of firing bar (82) at the portion of firing bar (82) within handle assembly (12) to bias firing bar (82) toward its unactuated position.

As the operator squeezes closure trigger (20) toward hand grip (38), slotted closure arm link (62) and closure links (56) move distally within receiving slot (84) of firing bar (82). This distal movement causes closure member (54) to correspondingly move distally. Likewise, firing bar (82) concurrently moves distally with closure member (54), because integral closure link pin (58), to which closure links (56) are attached, extends through receiving slot (84) in firing bar (82) (see FIG. 2A). Thereby, firing bar (82) is forced distally to form the staples (not shown) in the tissue and/or sever the tissue with knife (32) (see FIG. 6). Finally, the operator may fully squeeze firing trigger (22) toward hand grip (38) to "fire" surgical stapling instrument (10) and force firing bar (82) further distally to form the staples (not shown) and sever the tissue. This distal movement of firing bar (82) may also be referred to herein as "firing" the firing bar (82) to the actuated or "fired" position.

Upon operator release of one or both of closure and firing triggers (20, 22) while one or both of triggers (20, 22) is/are in a fired position, or in an intermediate position between the unactuated and fired positions, surgical stapling instrument (10) may be further configured to releasably lock in one of a variety of configurations. The operator may then release the hand grip (38) to free one or more hands for another task during the surgical procedure and, when desired, release surgical stapling instrument (10) from its locked position by release button (24). By way of example, surgical stapling instrument (10) has an intermediate closure detent position and a closure detent position. With respect to FIGS. 2A-2C, the top side of the slotted closure arm link (62) has a clamp sliding surface (102) that displays an intermediate detent (104) and a closure detent (106). A release pawl (108) slides on clamp sliding surface (102) and may engage intermediate and closure detents (104,106). Release pawl (108) has a laterally extending pawl lug (110) at its distal end.

Release pawl (108) is located within handle assembly (12) and is integrally formed with release button (24), which is situated exterior of handle housing (34) for manipulation by the operator. Release button (24) has a thumb rest (112) pivotally attached to handle housing (34) by a release trunnion (114). Release button (24) is biased outwardly from handle housing (34) and, therefore, release pawl (108) is biased downwardly toward clamp sliding surface (102) by a release spring (116). Release spring (116) is mounted to handle housing (34) by a spring retention pin (118) and is mounted to release button (24) by a button spring post (120). Slotted closure arm link (62) has an arcuate recess (122) located between intermediate and closure detents (104, 106). Resting within arcuate recess (122) for rotational movement are integrally connected left and right hand toggles (124). Each toggle (124) has a toggle arm (126) that is engageable with pawl lug (110).

In order to releasably lock handle assembly (12), toggle arms (126) from pawl lug (110) disengage from pawl lug (110) as closure trigger (20) is squeezed toward hand grip (38). Consequently, as toggle (124) continues to rotate in a clockwise direction, release pawl lug (108) rides up toggle arms (126) and, with continued motion of closure trigger (20), falls into one of intermediate and closure detents (104, 106), depending on the position of closure trigger (20) in use. As release pawl (108) rides up toggle arm (126), release pawl (108) rotates release button (24) clockwise. Release pawl (108) thereby falls into one of intermediate and detents (104, 106) and generates an audible clicking sound alerting the surgeon that one of the intermediate and closure positions have been reached.

In order to release handle assembly (12) from the intermediate or closure positions discussed herein, the surgeon depresses release button (24). In turn, release pawl (108) pivots about release trunnion (114) in a clockwise direction to dislodge pawl lug (110) from one of the intermediate and closure detents (104, 106). As pawl lug (110) is dislodged, pawl lug (110) rides on toggle arms (126) to another position, such as the unactuated position. Therefore, the operator may release closure and firing triggers (20, 22) such that each may return to the unactuated positions FIG. 1A and FIG. 3.

Surgical stapling instrument (10) of the present example includes each of handle frame plates (35, 36), push rod (50), closure member (54), and firing bar (82) extending continuously from handle assembly (12) to end effector (16), thereby defining shaft assembly (14) extending therebetween. Handle frame plates (35, 36), push rod (50), closure member (54), and firing bar (82) of surgical stapling instrument (10) provide merely a subset of elongated components extending distally from handle assembly (12) as shaft assembly (14). Alternatively, shaft assembly (14) may include additional components, such as an articulating joint, or may include a rearrangement of various components such that shaft assembly (14) may be modular relative to handle assembly (12). In any case, it will be appreciated that the invention is not intended to be limited to shaft assembly (14) described herein and may include various alternative arrangements for operatively connecting end effector (16) to handle assembly (12). Of course, handle assembly (12) and shaft assembly (14) may have a variety of other components, features, and operabilities, in addition to or in lieu of any of those noted above. Other suitable configurations for handle and shaft assemblies (12, 14) will be apparent to those of ordinary skill in the art in view of the teachings herein.

B. Illustrative End Effector

Figure 3:
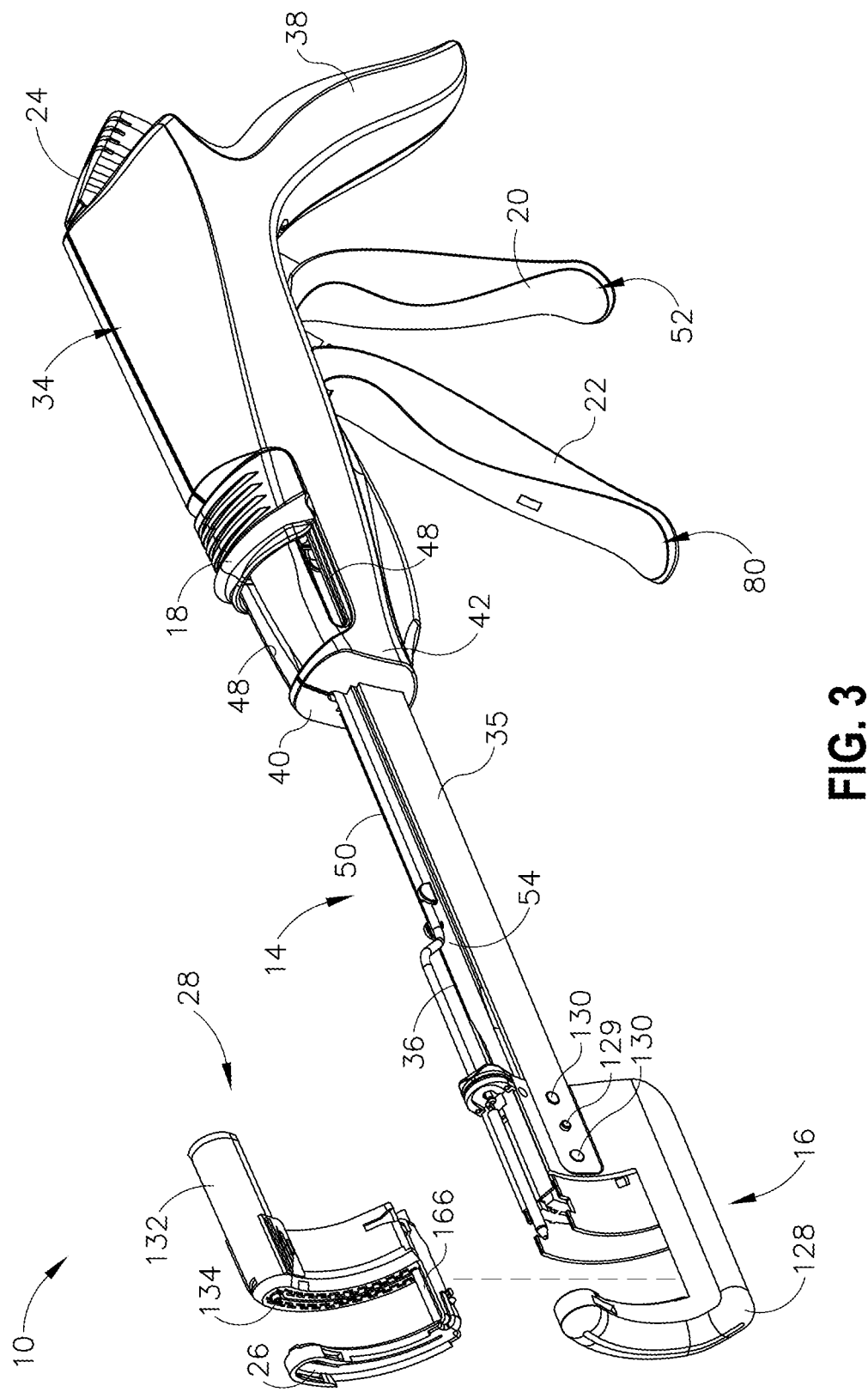
FIG. 3 depicts a partially exploded right front perspective view of the surgical stapling instrument of FIG. 1A showing the staple cartridge removed from a remainder of an end effector.
Figure 4:
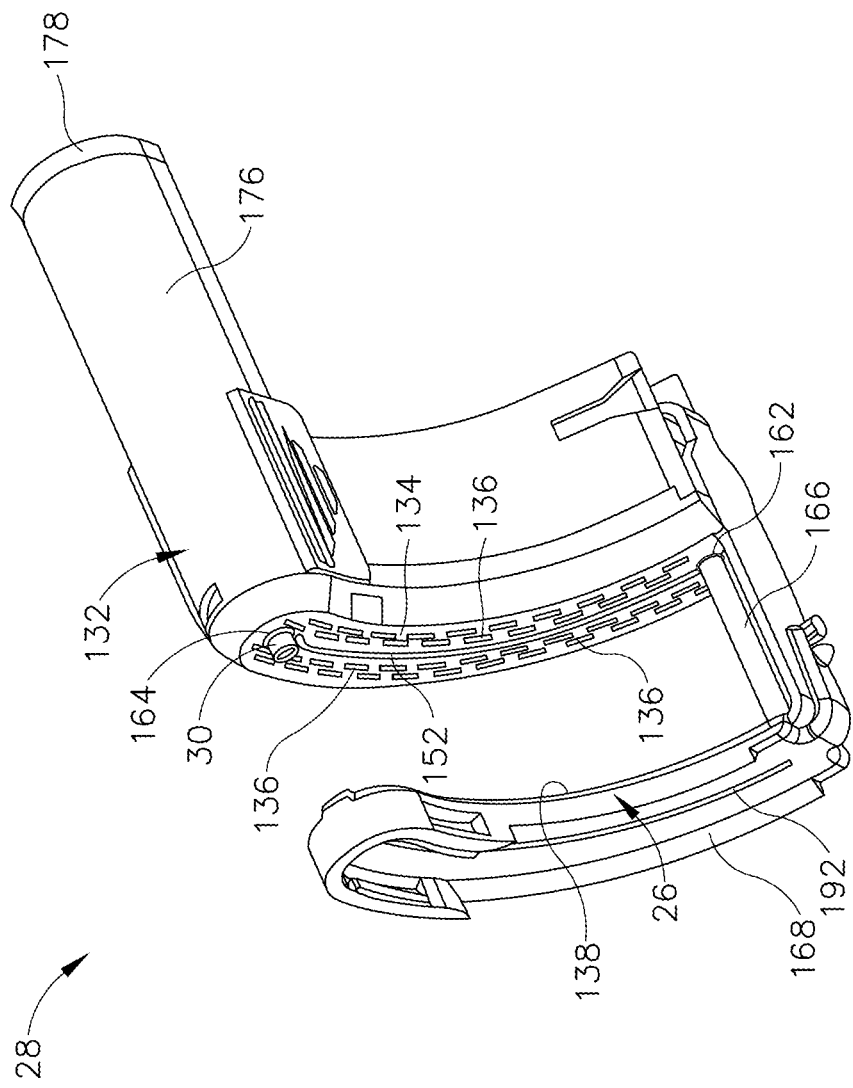
FIG. 4 depicts a right front perspective view of the staple cartridge of FIG. 3.
Figure 5:
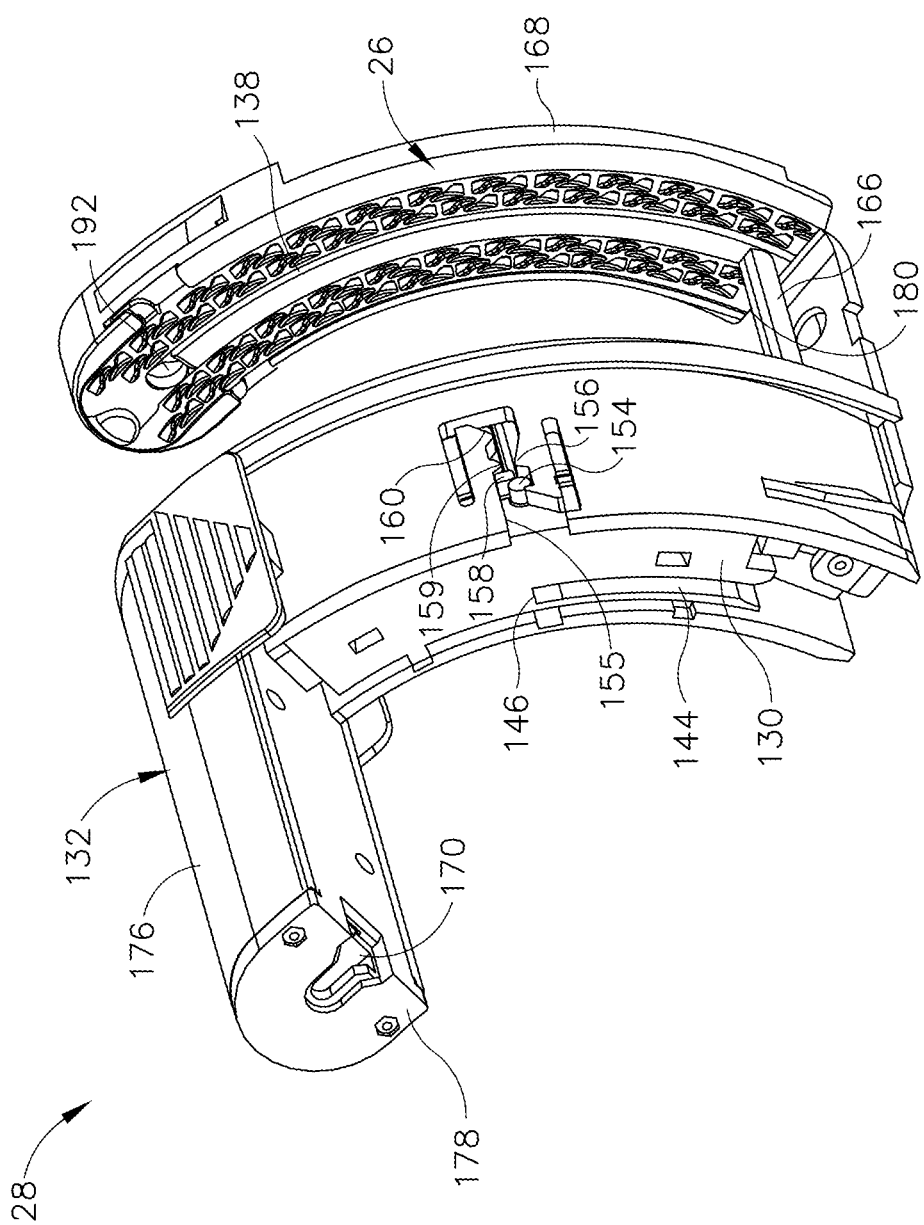
FIG. 5 depicts a rear perspective view of the staple cartridge of FIG. 3.

As also shown in FIGS. 3-5 and discussed briefly above, end effector (16) of the present example includes anvil (26), replaceable cartridge (28) including a plurality of staples (not shown) and knife (32) (see FIG. 6), and retainer pin (30). While end effector (16) of the present example is adapted for use in conjunction with replaceable cartridge (28) having various components, it will be appreciated that the concepts underlying the present invention could be applied to a variety of end effector and cartridge constructions for treating the patient.

End effector (16) provides a surgical fastening assembly that includes cartridge (28) received within a C-shaped supporting structure (128). The term C-shaped is used throughout the specification to describe the concave nature of supporting structure (128) and cartridge (28). The C-shaped construction facilitates enhanced functionality and access to tissue within the patient. The term "C-shaped" as used herein should be construed to include a variety of concave shapes that would similarly enhance the functionality of surgical stapling and cutting instruments. By way of example only, the C-shape of supporting structure (128) may be sized to promote access to the lower colon within the pelvic bowl of a patient, such as to perform a LAR in a proctocolectomy procedure.

Supporting structure (128) of end effector (16) is respectively attached to handle frame plates (35, 36) of shaft assembly (14) by a shoulder rivet (129) and posts (130) which extend from supporting structure (128) into receiving holes in handle frame plates (35, 36). The distal end of closure member (54) is disposed to receive cartridge (28) thereon for directing cartridge (28) to the closed configuration. Upon return of cartridge (28) from the closed configuration to the open configuration, cartridge (28) further includes a safety lockout mechanism (131) (see FIG. 7A) configured to inhibit inadvertently re-firing cartridge (28). Safety lockout mechanism (131) will be discussed below in additional detail.

Cartridge (28) includes anvil (26) coupled to a cartridge housing (132). Cartridge (28) also includes retaining pin (30) and a tissue contacting surface (34), which defines a plurality of staple-containing slots (136) in staggered formation in one or more rows on either side of knife (32) (see FIG. 6). Staples (not shown) are fired from cartridge housing (132) against a staple-forming surface (138) of anvil (26) that faces tissue-contacting surface (134) of cartridge housing (132). Cartridge (28) may also include a removable retainer (not shown) for storage between anvil (26) and tissue contacting surface (34) prior to and/or after use in order to inhibit unintended contact with various portions of cartridge (28).

Figure 6:
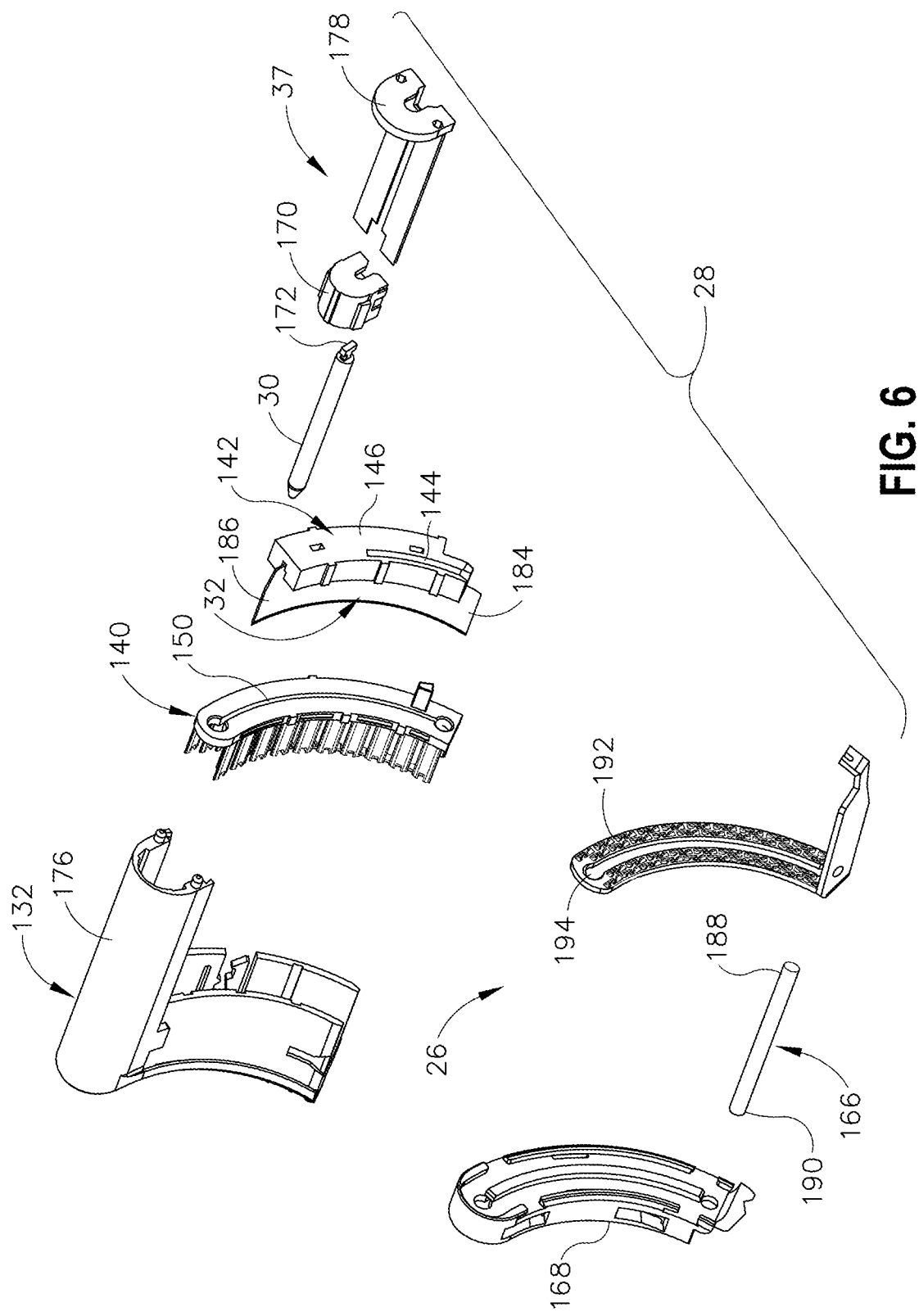
FIG. 6 depicts an exploded rear perspective view of the staple cartridge of FIG. 3.

As shown in FIGS. 4-6, cartridge (28) includes a staple driver assembly (140) within cartridge housing (132) and proximally positioned behind the plurality of staples (not shown) within staple-containing slots (136). Driver assembly (140) of the present example is formed as a unitary structure of a plurality of staple drivers (141). Thus, the term "assembly" is not intended to be limited to an assembly of individual components but may also include integrally formed components with unitary structures. Driver assembly (140) is configured to push the staples (not shown) respectively out of staple containing slots (136) and toward anvil (26) for formation. A knife holder (142) is disposed immediately proximal of driver assembly (140) in cartridge housing (132) and defines a slot (144) and ledge (146) for interaction with a knife retractor hook (148) (see FIG. 10B), which is discussed below in greater detail. Knife holder (142) is attached to knife (32) such that knife (32) extends distally from knife holder (142) through a slot (150) in driver assembly (140) and through another slot (152) in cartridge housing (132). Although knife (32) is disclosed as being within cartridge housing (132) in the present example, other configurations may also be used. For example, it will be appreciated that cartridge (28) may alternatively not include knife (32) for alternative treatments.

Knife holder (142) has a detent post (154) that extends through a slot (155) in cartridge housing (132). Detent post (154) is positioned in order to contact a detent protrusion (156) of cartridge slot (155) during the longitudinal travel of knife (132) and knife holder (142). Similarly, driver assembly (140) has a detent post (158) positioned in order to contact proximal and distal detent protrusions (159, 160) of cartridge slot (155).

Knife (32) and slots (150, 152) are positioned such that there is at least one row of staples (not shown) on either side of knife (132). In some versions, two rows of staple slots (136) containing respective rows of staples (not shown) are provided on each side of slot (152) of cartridge housing (132).

Cartridge housing (132) defines two longitudinally extending, generally circular holes (162, 164) at respective ends of knife slot (152). More particularly, hole (162) at a lower portion of cartridge housing (132) is shaped and dimensioned to receive a guide pin (166) through cartridge housing (132). Hole (164) at an upper portion of cartridge housing (132) is shaped and dimensioned to slidably receive retaining pin (30) through cartridge housing (132). Staple slots (136) of the present example are arranged such that the staples (not shown) laterally extend past the generally circular holes (162, 164).

Anvil (26) of the present example includes a plastic cutting washer (168) and a metallic staple-forming surface (138). Anvil (26) is disposed to maintain staple-forming surface (138) in alignment with the staples (not shown) to receive and form the staples (not shown) thereon. Retaining pin (30) is connected to a couplet (170) by a circumferential slot (172) in retaining pin (30) and a groove (not shown) in couplet (170). Couplet (170) is disposed within an arm (176) of cartridge housing (132) and is secured to arm (176) by an end cap (178).

Guide pin (166) and retaining pin (30) include respective slots (180, 182) (see also FIGS. 8-9) into which lower and upper ends (184, 186) of knife (32) are slidably disposed. A proximal end (188) of guide pin (166) is connected to anvil (26), whereas a distal end (190) of guide pin (166) extends from cartridge housing (132) and extends through a slot (192) in anvil (26). Cutting washer (168) slips onto anvil (26) via groove (194). Thereby, cutting washer (168) is configured to trap guide pin (166) in the opening formed by slot (192) in anvil (26) and a cutting surface (157) of anvil (26) for connecting anvil (26) to cartridge housing (132).

Figure 7A:
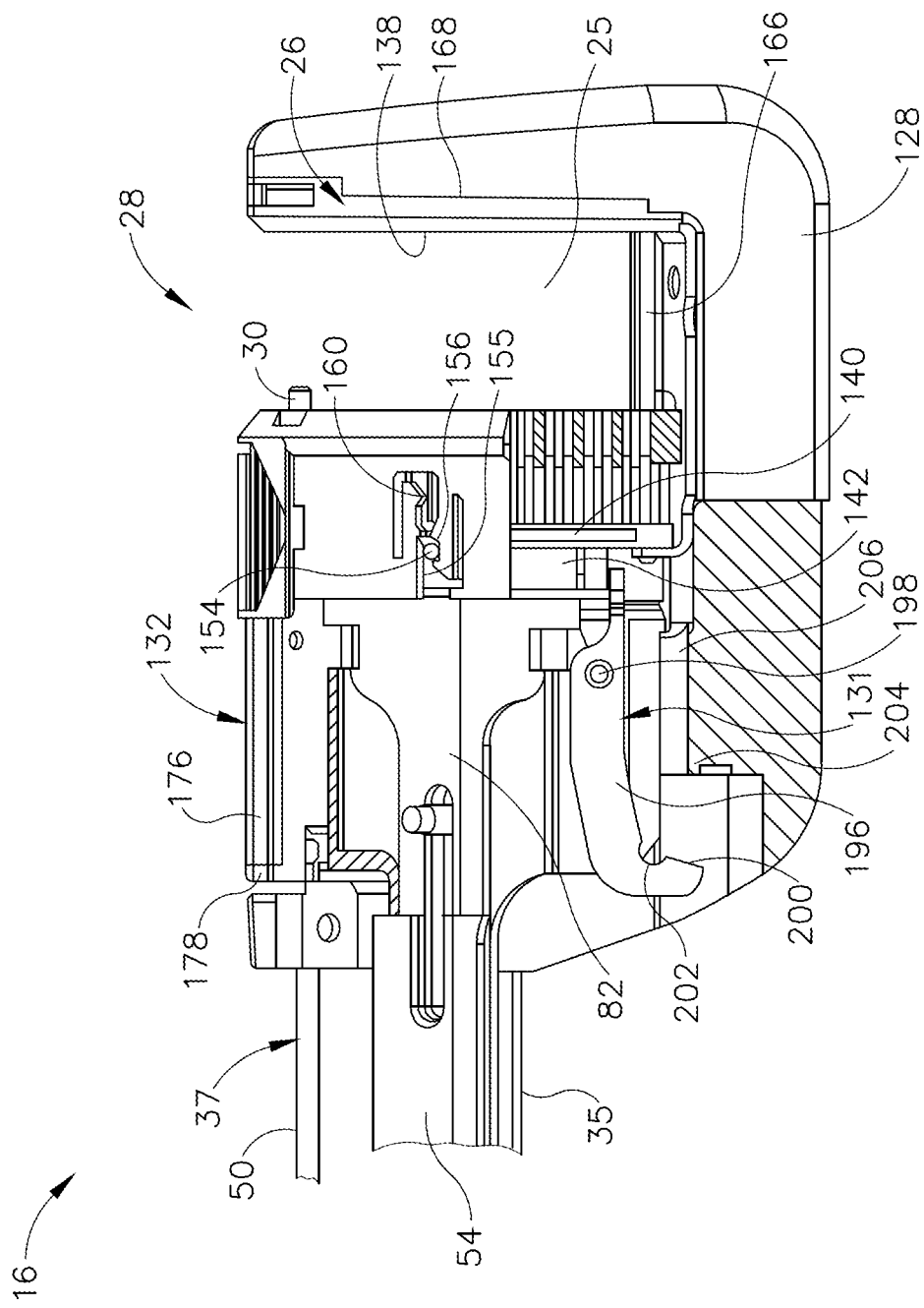
FIG. 7A depicts a left side elevational view of the end effector of FIG. 1A with various components removed for clarity.

Lockout mechanism (131) is shown in FIG. 7A in greater detail. Lockout mechanism (131) is configured to inhibit full proximal movement of cartridge housing (132) to its unactuated position after firing. To this end, lockout mechanism (131) of the present example includes a lockout lever (196) that is pivotally mounted to the distal end of closure member (54) by a pin (198). Lockout lever (196) is spring biased toward the proximal end portion of supporting structure (128) by a spring (not shown). A proximal end portion of lockout lever (196) has a cam surface (200) and a locking groove (202). Supporting structure (128) of end effector (16) also has a ledge (204) that is configured to cooperate with locking groove (202) when lockout mechanism (131) is engaged. In contrast, supporting structure (128) has a base surface (206) configured to cooperate with cam surface (200) when lockout lever (131) is not engaged.

C. Illustrative Use of Surgical Stapler

In the present example, cartridge (28) is driven toward anvil (26) via closure member (54) until reaching the closed configuration with tissue positioned between cartridge (28) and anvil (26) as discussed above with respect to handle assembly (12). From the closed configuration, knife (32) and staple driver assembly (140) are further moved toward anvil (26) via firing bar (82) to form staples (not shown) in the tissue, fluidly seal the tissue, and sever the tissue for treating the patient. While actuation of cartridge (28) includes stapling and severing tissue in this example, it will be appreciated that one or more of these steps may be omitted from treatment as desired by the operator. Moreover, it will be appreciated that surgical stapling instrument (10) may be reconfigured to perform these steps simultaneously or sequentially as desired. For example, actuation of firing bar (82) causes driver assembly (140) and knife (32) to move distally toward anvil (26) in the present example. Alternatively, surgical stapling instrument (10) may be reconfigured to selectively fire one of staples (not shown) or knife (32), or selectively fire staples (not shown) and then knife (32), or vice versa. It should therefore be understood that the invention is not intended to be limited to the particular operation of surgical stapling instrument (10) or the associated treatment.

Figure 7B:
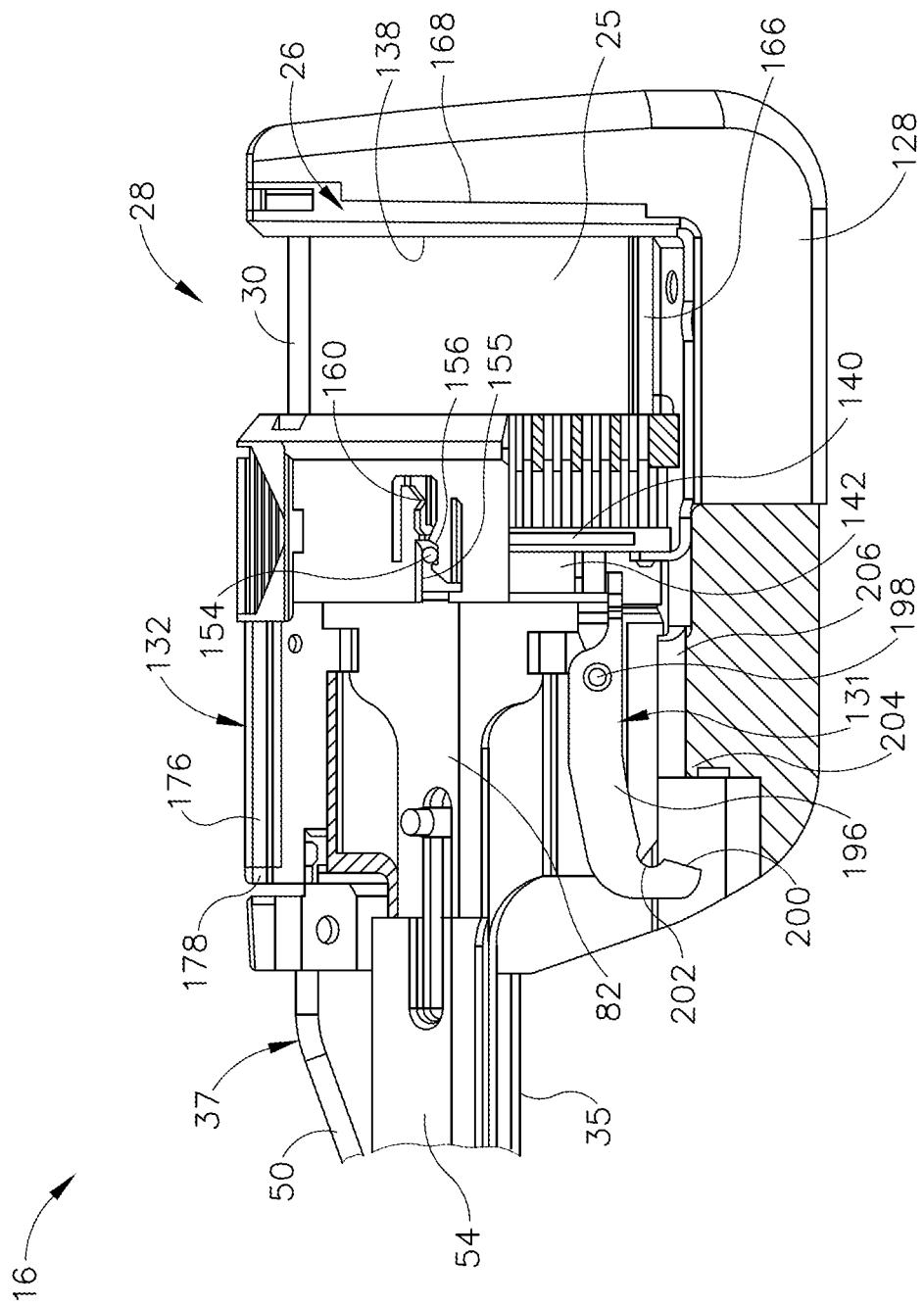
FIG. 7B depicts a left side elevational view of the end effector of FIG. 1A with various components removed for clarity, and with the pin actuation mechanism in the closed position and the staple cartridge in the open position.

As shown in FIG. 7A, cartridge (28) is spaced proximally from anvil (26) to receive tissue within gap (25) in the open configuration. With tissue received between cartridge (28) and anvil (26), the operator manually directs push rod (50) distally via slide (18) as discussed above and shown in FIG. 7B. Push rod (50) is operatively connected to couplet (70) (see FIG. 6), which is connected to retaining pin (30). Thus, distally translating push rod (50) similarly translates retaining pin (30) to extend from cartridge (28) to anvil (26) and capture tissue between retaining pin (30) and guide pin (166).

Figure 7C:
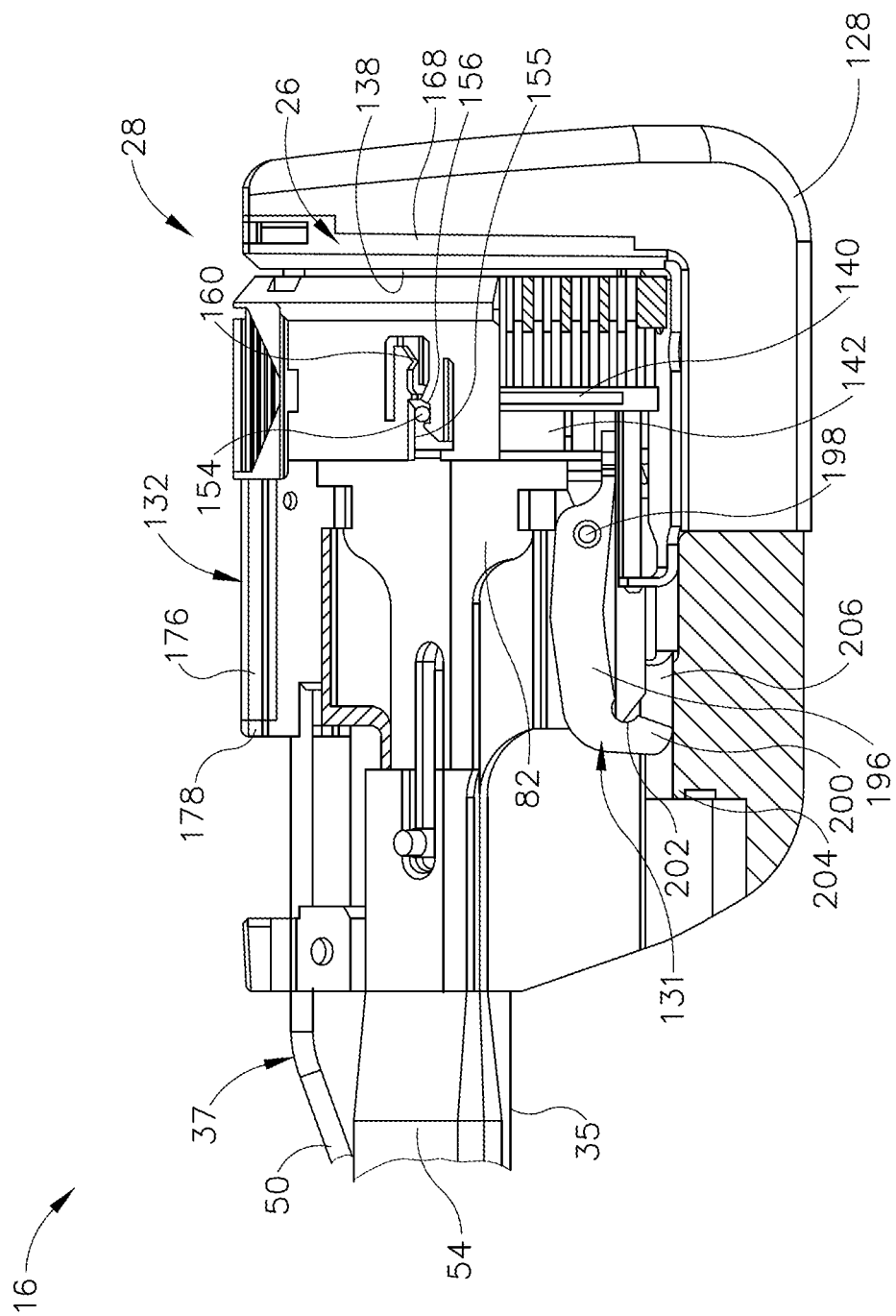
FIG. 7C depicts a left side elevational view of the end effector of FIG. 1A with various components removed for clarity, and with the pin actuation mechanism in the closed position and the staple cartridge in the closed position via actuation of the closure mechanism.
Figure 7D:
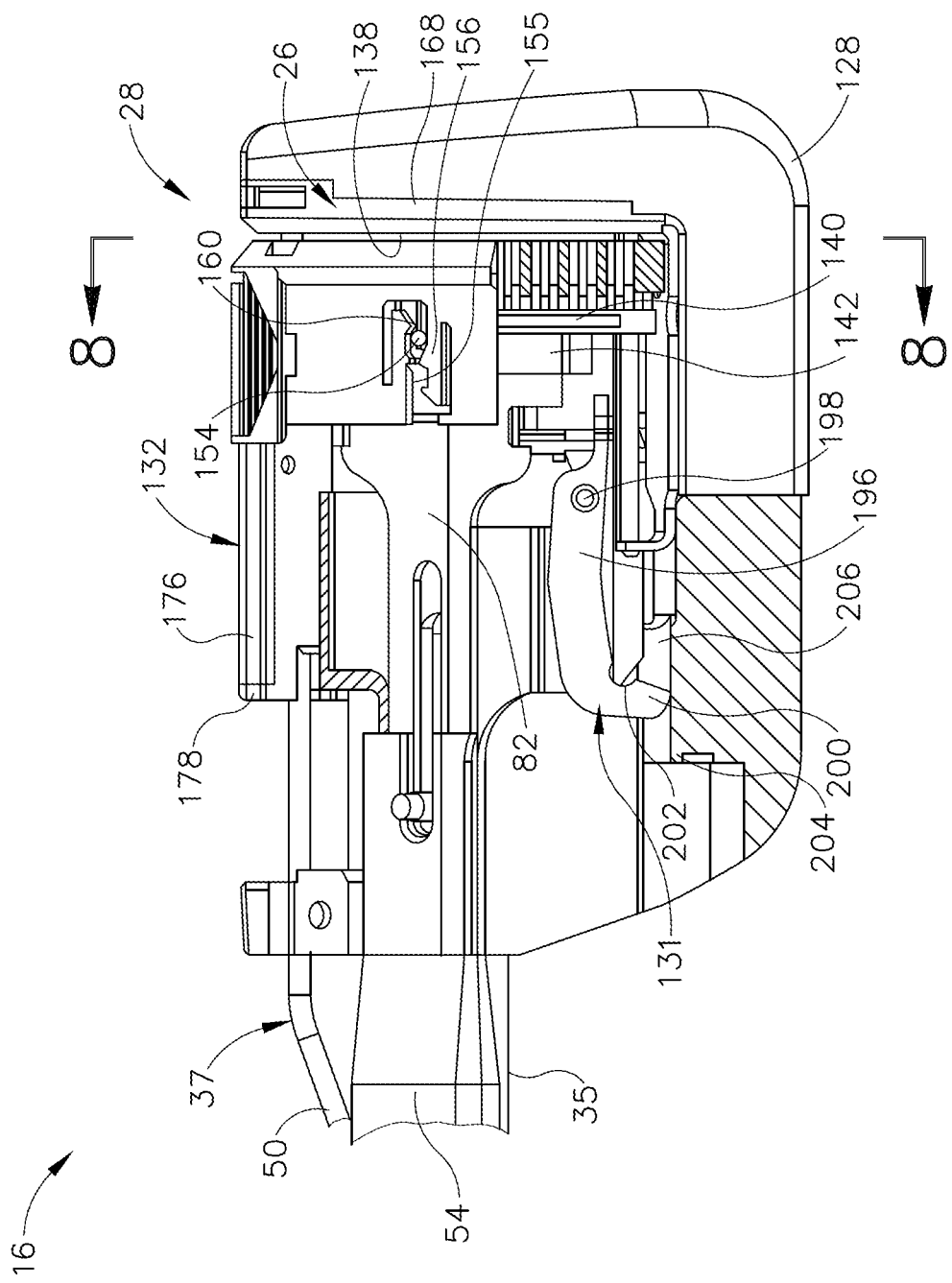
FIG. 7D depicts a left side elevational view of the end effector of FIG. 1A with various components removed for clarity, and with the pin actuation mechanism and the staple cartridge in the closed positions and the firing trigger in the fired position for stapling and cutting tissue of a patient.
Figure 8:
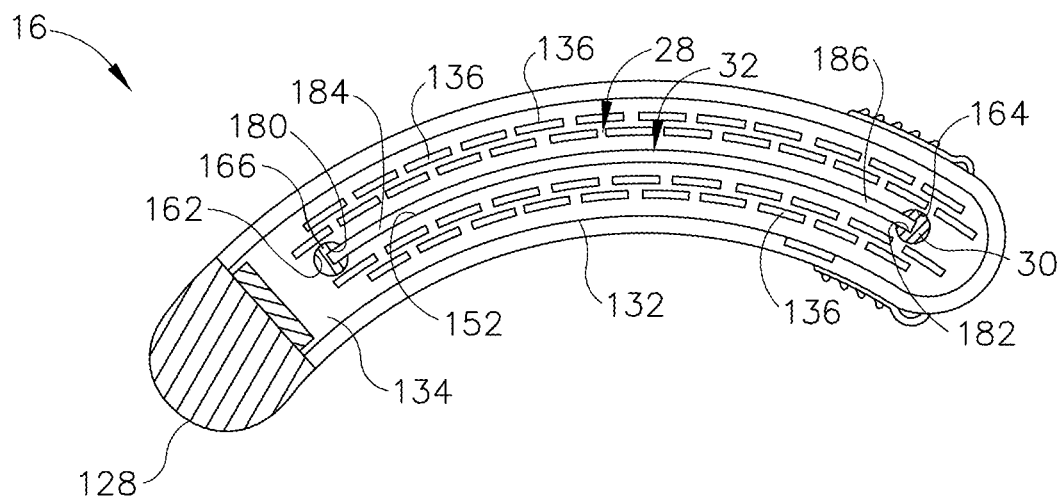
FIG. 8 depicts a cross-sectional view of the end effector of FIG. 7D, taken along section line 8-8 of FIG. 7D.
Figure 9:
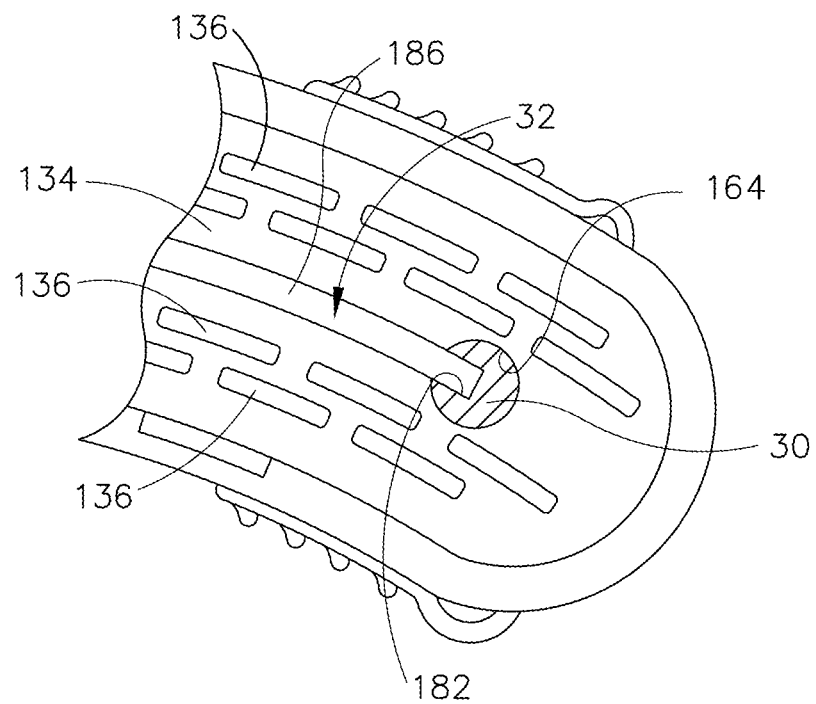
FIG. 9 depicts an enlarged cross-sectional view of a portion of the end effector of FIG. 8.

As shown in FIG. 7C, manipulation of closure trigger (20) (see FIG. 1C) forces closure member (54) to translate distally relative to supporting structure (128) of end effector (16). Closure member (54) supports cartridge (28) thereon such that distal translation of closure member (54) similarly moves firing bar (82) and cartridge (28) toward anvil (26). With cartridge (28) in the closed configuration and the tissue effectively captured in the end effector (16), the operator manipulates firing trigger (22) (see FIG. 1D) toward anvil (26) to the fired position. Distal translation of firing bar (82) causes firing bar (82) to engage knife holder (142), which supports both driver assembly (140) and knife (32) extending through driver assembly (140) as shown in FIG. 7D. In turn, driver assembly (140) directs staples (not shown) from staple slots (136) and against staple-forming surface (138) to form the staples (not shown) within the tissue for fluidly sealing the tissue. As the staples (not shown) are formed, knife (32) continues to translate distally through tissue and into anvil (26) to sever the fluidly sealed tissue. FIGS. 8-9 illustrate the fired cartridge (28) in greater detail, with knife (32) guided along cartridge housing slot (152), guide pin slot (180); and with retaining pin slot (182) between rows of staple slots (136) toward anvil (26).

Figure 10A:
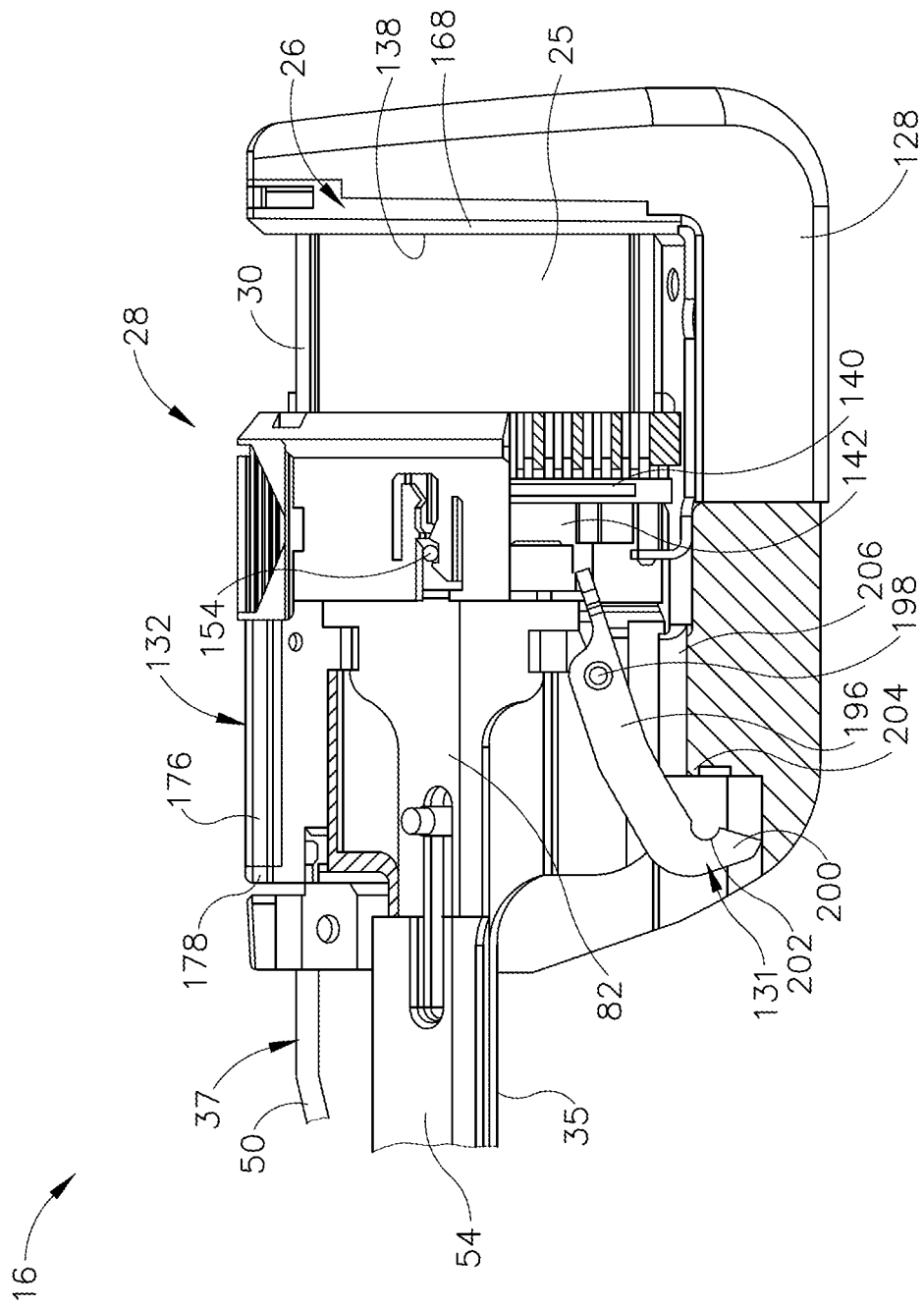
FIG. 10A depicts a left side view of the end effector of FIG. 1A, with various components removed for clarity, with the staple cartridge returned to the open position after actuating the firing trigger.
Figure 10B:
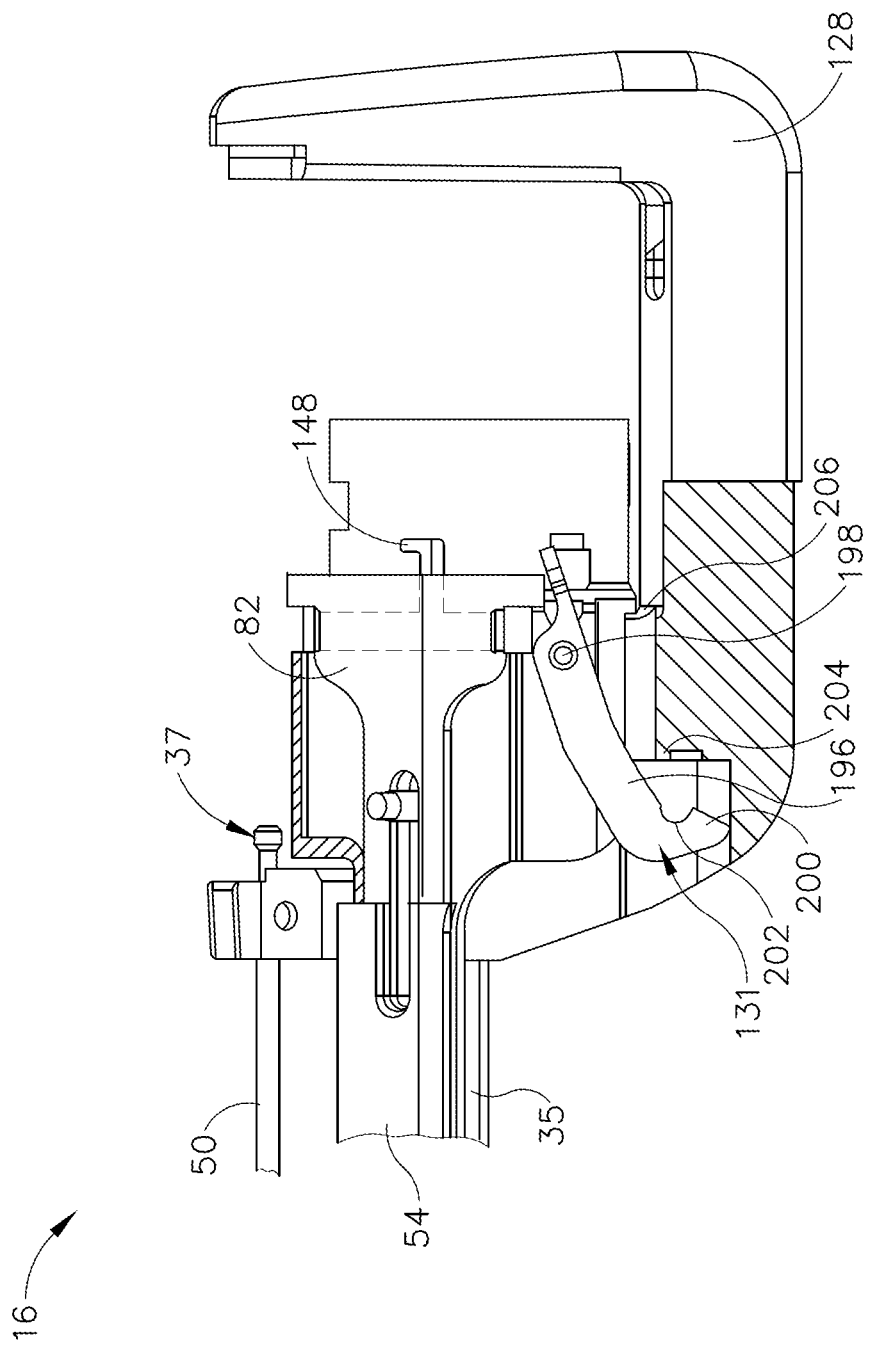
FIG. 10B depicts a left side view of the end effector of FIG. 1A, with various components removed for clarity, with the staple cartridge removed from the remainder of the end effector.

Once fired, the operator may depress release button (24) (see FIG. 2C) and withdraw closure member (54) and firing bar (82) proximally from the actuated, fired position to the unactuated position shown in FIGS. 10A-10B. More particularly, retractor hook (148) engages knife holder (142) to pull knife (32) proximally. At approximately the same time, as cartridge (28) translates proximally with closure member (54), lockout lever (196) of lockout mechanism (131) engages cartridge housing (132) to hold cartridge housing (132) in position. Thereby, the continued pull of knife (32) retracts knife (32) within cartridge housing (132) to inhibit unintended contact by operator with knife (32). Cartridge (28) may then be removed from supporting structure (128) of end effector (16), discarded, and replaced for further treatment if so desired. Of course, various suitable settings and procedures in which surgical stapling instrument (10) may be used will be apparent to those of ordinary skill in the art in view of the teachings herein.

It should also be understood that any other components or features of surgical stapling instrument (10) may be configured and operable in accordance with any of the various references cited herein. Additional illustrative modifications that may be provided for surgical stapling instrument (10) will be described in greater detail below. Various suitable ways in which the below teachings may be incorporated into surgical stapling instrument (10) will be apparent to those of ordinary skill in the art. Similarly, various suitable ways in which the below teachings may be combined with various teachings of the references cited herein will be apparent to those of ordinary skill in the art. It should also be understood that the below teachings are not limited to surgical stapling instrument (10) or devices taught in the references cited herein. The below teachings may be readily applied to various other kinds of instruments, including instruments that would not be classified as surgical staplers. Various other suitable devices and settings in which the below teachings may be applied will be apparent to those of ordinary skill in the art in view of the teachings herein.

II. Illustrative Surgical Stapler with Alternative Clamp Force Sensors

Generally speaking, when tissue is clamped in an end effector, the thickness and position of the tissue can affect the ability of the stapler to properly cut and staple the tissue. If the tissue is too thick and/or is improperly positioned in the end effector, the tissue may be incorrectly cut or the staples may not be implanted or formed correctly which can potentially result in a problematic surgical site, such as where tissue is cut by knife (32) but not fully sealed along the cut line by properly formed staples. It may therefore be desirable to detect improper clamping of tissue and to notify a user accordingly to prevent the tissue from being improperly cut and/or stapled. The following description relates to examples of different features that may be incorporated into an end effector or a cartridge to achieve this desired functionality. While these examples are provided separate from each other, the features described in any of the following examples may be combined with the features described in other examples described below. Thus, the below-described features may be combined in various permutations as will be apparent to those skilled in the art in view of the teachings herein.

A. Force Sensing Link Between Actuator Bar and Handle

Figure 11:
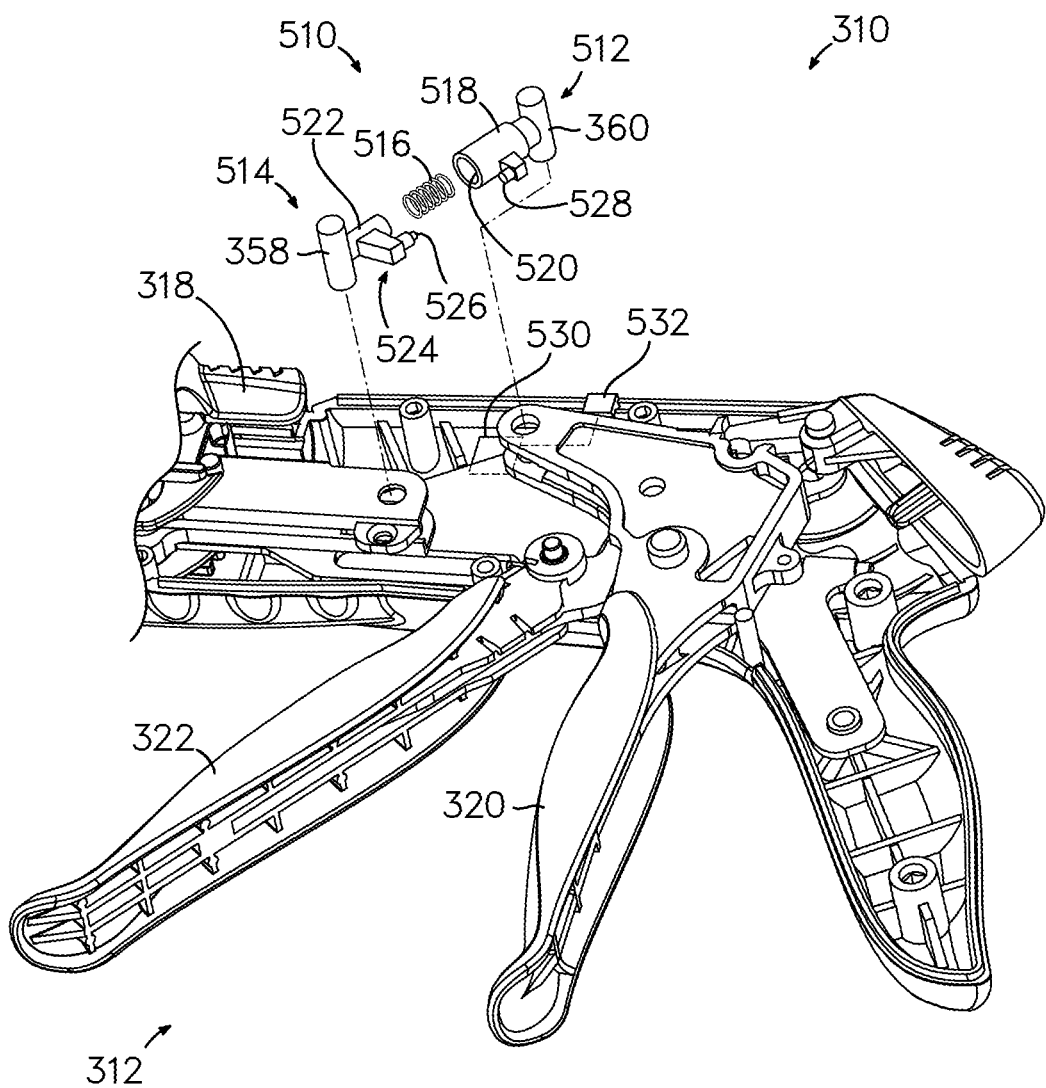
FIG. 11 depicts a perspective view of a handle assembly of another illustrative surgical stapling instrument, with various components removed for clarity.
Figure 12A:
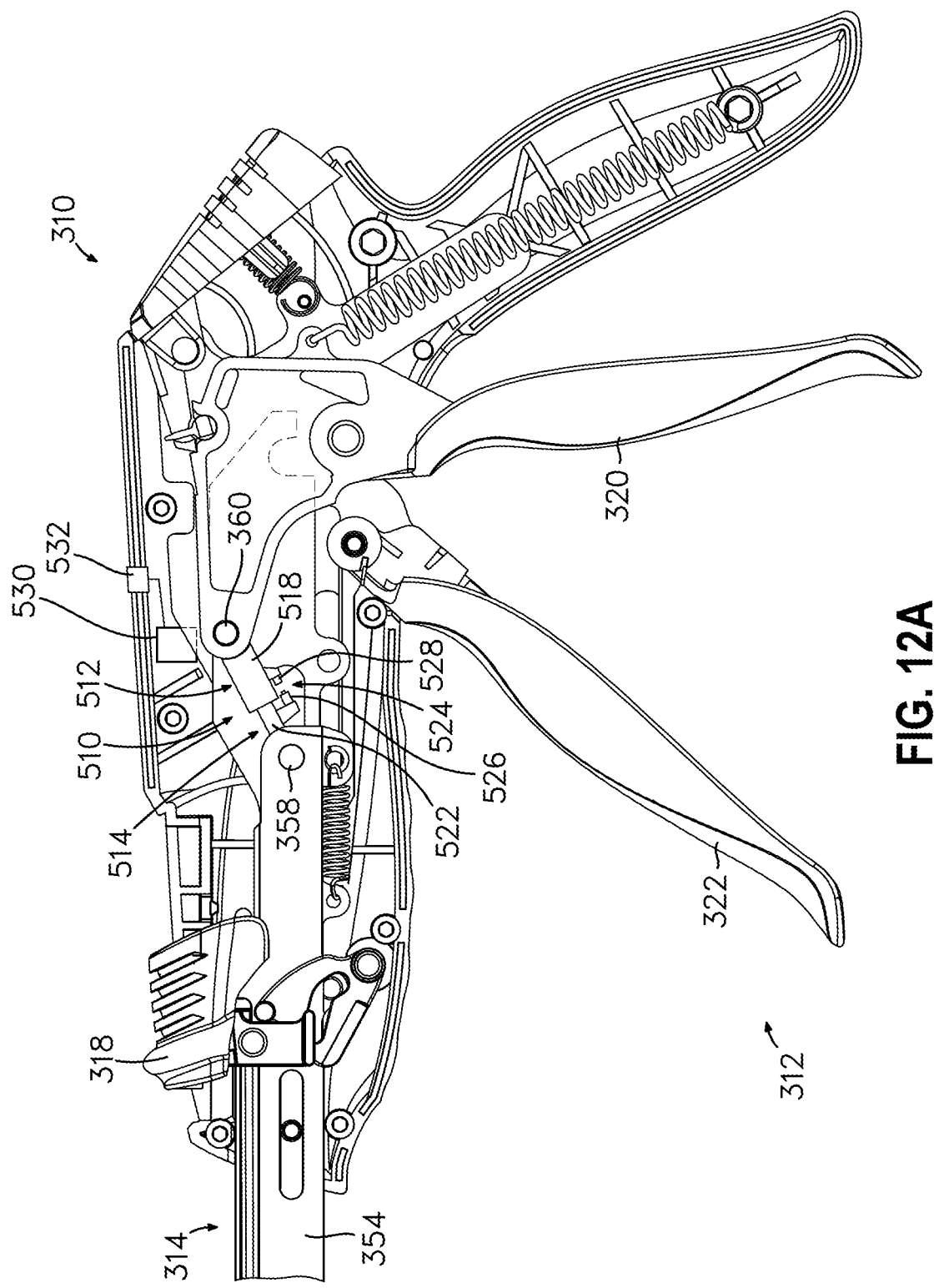
FIG. 12A depicts a right side elevational view of the handle assembly of the surgical stapling instrument of FIG. 11, with various components removed for clarity, and with the pin actuation mechanism in a closed position and the staple cartridge in the open position.
Figure 12B:
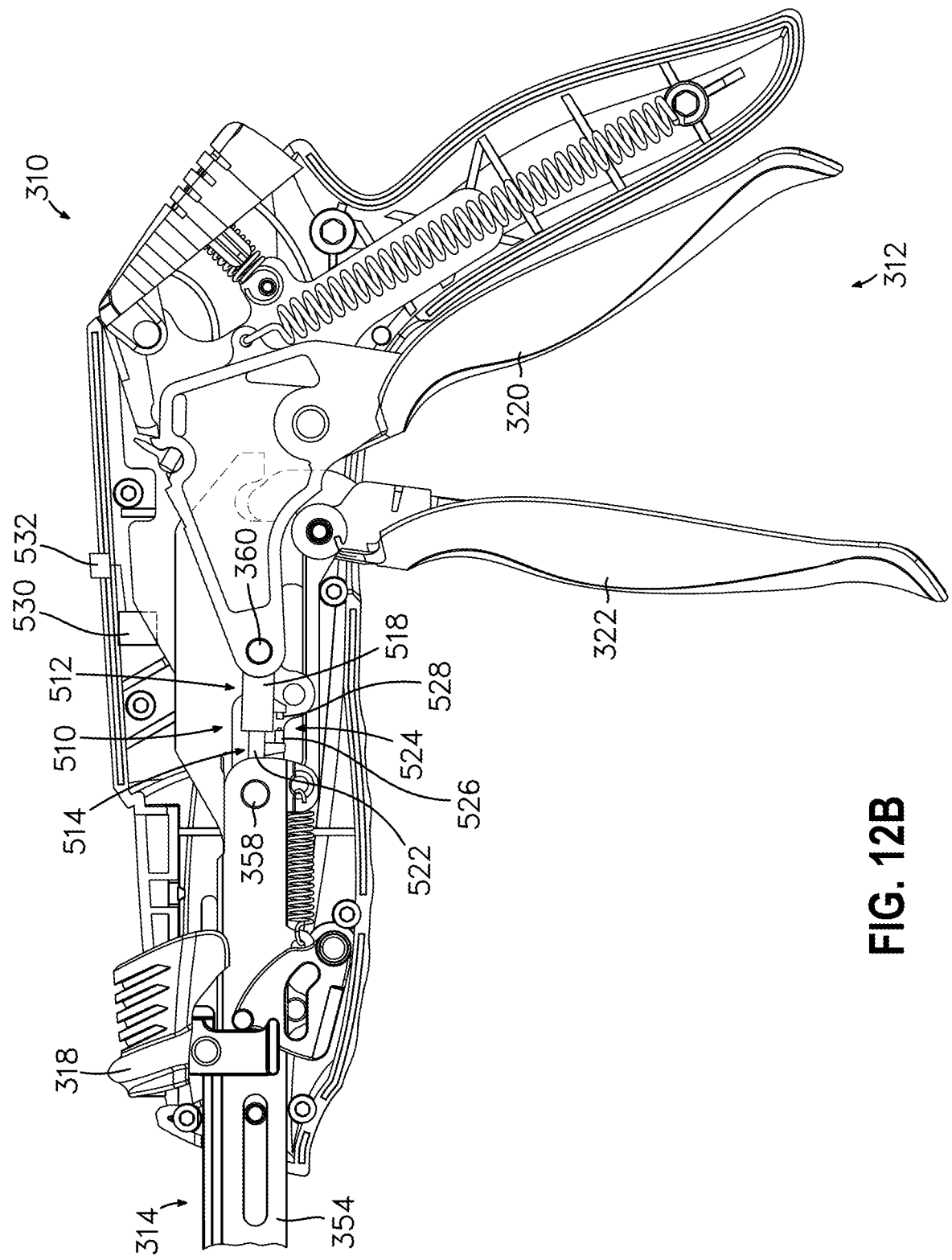
FIG. 12B depicts a right side elevational view of the handle assembly of the surgical stapling instrument of FIG. 11, with various components removed for clarity, and with the pin actuation mechanism in the closed position and the staple cartridge in the closed position via actuation of the closure mechanism.
Figure 12C:
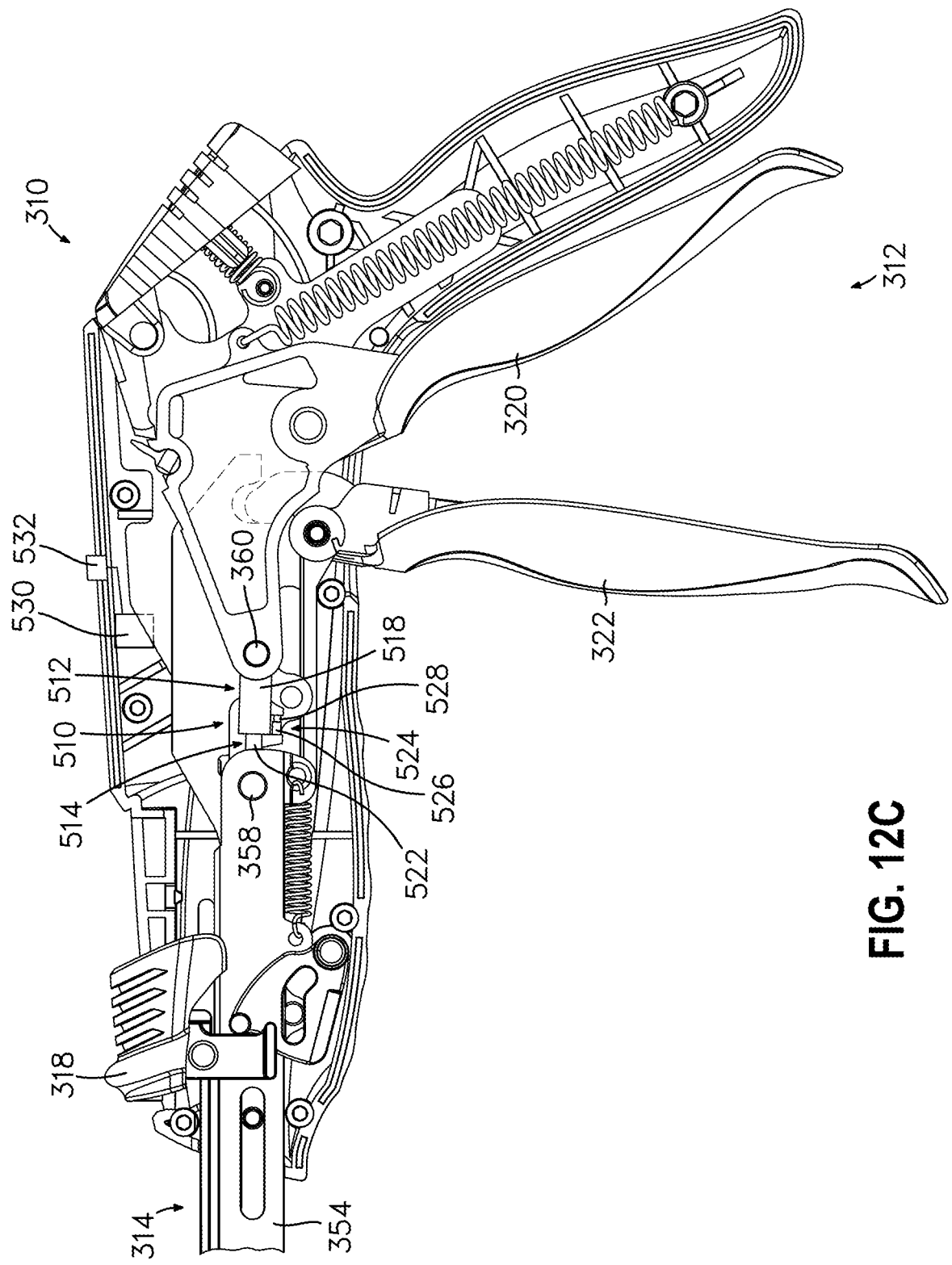
FIG. 12C depicts a right side elevational view of the handle assembly of the surgical stapling instrument of FIG. 11, with various components removed for clarity, and with the pin actuation mechanism and the staple cartridge in the closed positions and the firing trigger in the fired position for stapling and cutting tissue of a patient.

FIGS. 11-12C show another illustrative surgical stapling instrument (310) that is generally similar to surgical stapling instrument (10) described above except as otherwise described below. Surgical stapling instrument (310) includes a handle assembly (312), a shaft assembly (314), and an end effector (e.g., 16) distally projecting from shaft assembly (314). Handle assembly (312) includes a saddle shaped slide (318), a closure trigger (320), and a firing trigger (322) in communication with end effector via shaft assembly (314). Translating slide (318) distally toward the end effector slides a retaining pin (e.g., 30) of the end effector distally (see e.g., FIG. 1B) for capturing the tissue between anvil (e.g., 26) and cartridge (e.g., 28). Sequentially actuating closure trigger (320) and firing trigger (322) respectively compresses the tissue between the anvil and cartridge in a closed configuration and then forms a plurality of staples within the tissue and severs the tissue with a knife.

A closure member (354) extends distally from handle assembly (312), through shaft assembly (314), and into end effector for operably coupling with the cartridge. A proximal end portion of closure member (354) is operatively coupled to closure trigger (320) by a sensing link (510) that is pivotally attached to the closure member (354) at opposite ends. As will described in further detail below, sensing link (510) can serve as a clamp force sensor. As illustrated in FIGS. 12A and 12B, closure trigger (320) is operable to be pivoted between a released position (FIG. 12A) and an actuated position (FIG. 12B) which can facilitate corresponding sliding of closure member (354) to facilitate selective clamping of tissue at the end effector, as described above. In particular, as illustrated in FIG. 12A, when closure trigger (320) is in the released position, the closure member (354) is in a retracted position which opens the cartridge relative to the anvil to allow for tissue to be provided therebetween. As illustrated in FIG. 12B, when the closure trigger (320) is pivoted to the actuated position, the closure member is slid to a fully extended position which urges the cartridge towards the anvil to facilitate clamping of the tissue therebetween.

Sensing link (510) is a spring actuated link and is configured to detect the force exerted between the closure trigger (320) and the closure member (354). As will be described in further detail below, this detected force can be a function of the clamping force exerted by the cartridge on tissue and can be used to determine whether tissue is improperly clamped to facilitate generation of a notification accordingly.

As illustrated in FIG. 11, sensing link (510) includes a support (512) and a plunger (514) that are slidable relative to each other and are biased apart by a spring (516). Support (512) includes a link pin (360) and a sleeve (518) that defines a receptacle (520). Plunger (514) includes a link pin (358) and a rod (522). Link pins (358, 360) operably couple sensing link (510) to closure member (354) and closure trigger (320). Spring (516) is disposed in receptacle (520) and rod (522) contacts spring (516) and extends partially into receptacle (520) to compress spring (516) within receptacle (520) such that spring (516) biases support (512) and plunger (514) apart. Rod (522) is slidable relative to sleeve (518) which allows sensing link (510) to be selectively compressed against the biasing of spring (516).

Sensing link (510) further includes a switch assembly (524) that is selectively activated when support (512) and plunger (514) are compressed together beyond a predefined distance, as will be described in further detail below. Switch assembly (524) includes a switch (526) coupled with rod (522) and a pin (528) coupled with sleeve (518) and substantially aligned with switch (526). Sufficient compression of sensing link (510) can cause the pin (528) to depress switch (526) to facilitate activation thereof.

The response of sensing link (510) to clamping force applied to the tissue by the cartridge via closure trigger (320) can depend upon whether the tissue is properly clamped. For example, as illustrated in FIG. 12B, when the tissue is properly clamped, the clamping force applied to the tissue by closure trigger (320) and the cartridge is insufficient to overcome the biasing force of the spring (516) that is exerted on the rod (522) to prevent compression of sensing link (510). As a result, the sensing link remains substantially uncompressed such that the switch (526) remains open as an indication that the tissue is properly clamped. However, when the tissue is improperly clamped, as illustrated in FIG. 12C, the clamping force applied to the tissue by closure trigger (320) and the cartridge exceeds the biasing force of the spring (516) that is exerted on the rod (522) which causes the closure member (354) to be extended slightly rearwardly enough to compress the sensing link (510) and depress the switch (526) as an indication that the tissue is improperly clamped.

A microprocessor (530) is communicatively coupled to switch (526) and a feedback generator (532). Microprocessor (530) may be embodied as any type of processor capable of performing the functions described herein. For example, microprocessor (530) may be embodied as a single or multi-core processor, a digital signal processor, a microprocessor, a general purpose central processing unit (CPU), a reduced instruction set computer (RISC) processor, a processor having a pipeline, a complex instruction set computer (CISC) processor, an application specific integrated circuit (ASIC), a programmable logic device (PLD), a field programmable gate array (FPGA), or other processor or processing/controlling circuit or controller. Feedback generator (532) may be embodied as any type of generator processor capable of generating a notification, such as for example, a light, a speaker, a display, or some combination thereof. Switch (526), microprocessor (530), and feedback generator (532) can be powered from a remote power source connected to surgical stapling instrument (310) via a cable (not shown) or from an internal power source located onboard surgical stapling instrument (310), such as a battery, for example.

Microprocessor (530) is configured to facilitate generation of an audible notification and/or a visual notification from feedback generator (532), as a function of the status of switch (526), to warn the user when the tissue is improperly clamped. For example, when the tissue is properly clamped, such that switch (526) is deactivated, the microprocessor (530) recognizes that the switch (526) is deactivated and provides a suitable notification via feedback generator (532) that indicates to a user that the tissue is properly clamped that the surgical stapling instrument (310) is ready to fire. In some examples, microprocessor (530) can deactivate the feedback generator (532) to provide such indication. In an alternative example, microprocessor (530) can activate the feedback generator (532) to generate notification that is understood to indicate that the surgical stapling instrument (310) is ready to fire, such as a green light. When the tissue is improperly clamped, such that switch (526) is activated, the microprocessor (530) recognizes that the switch (526) is activated and can provide a suitable notification via feedback generator (532) that warns the user that the tissue is improperly clamped to prevent of the surgical stapling instrument (310). It is to be appreciated that various characteristics of spring (516), such as spring constant, can be selected to achieve generation of the indication at a desired clamping force in order to accommodate a particular surgical setting. It is also to be appreciated that sensing link (510) can comprise any of a variety of suitable alternative sensors that facilitate detection of excessive clamping force, such as, for example, a Hall-effect sensor or an optical sensor. In some instances, microprocessor (530) is configured to log certain information during the procedure in order to provide a historical record for the surgical stapling instrument (310) that can be accessed later to review the performance of the surgical stapling instrument (310).

Figure 13:
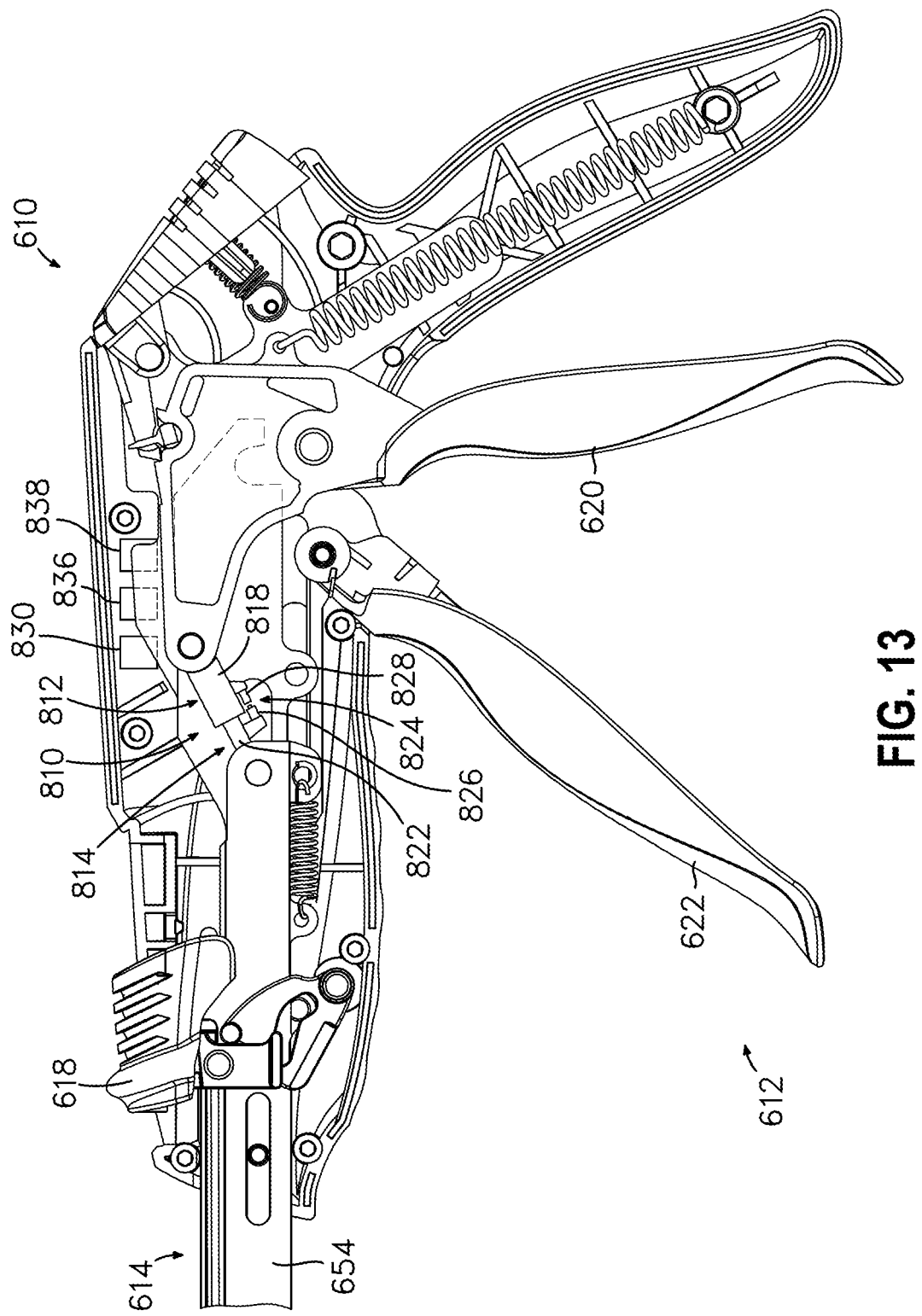
FIG. 13 depicts a right side view of a handle assembly of another illustrative surgical stapling instrument, with various components removed for clarity.

FIG. 13 shows an illustrative surgical stapling instrument (610) that is generally similar to surgical stapling instrument (310) described above except as otherwise described below. Surgical stapling instrument (310) includes a handle assembly (612), a shaft assembly (614), and an end effector (e.g., 16) distally projecting from shaft assembly (614). Handle assembly (612) includes a saddle shaped slide (618), a closure trigger (620), and a firing trigger (622) in communication with end effector via shaft assembly (614). A closure member (654) extends distally from handle assembly (612), through shaft assembly (614), and into end effector for operably coupling with the cartridge. A proximal end portion of closure member (654) is operatively coupled to closure trigger (620) by a sensing link (810) that is pivotally attached to the closure member (354) at opposite ends.

Sensing link (810) includes a support (812), a plunger (814), and a switch assembly (824). Switch assembly (824) includes a switch (826) coupled with rod (822) and a pin (828) coupled with sleeve (818) and substantially aligned with switch (826). A microprocessor (830) is communicatively coupled to switch (826). Microprocessor (830) is communicatively coupled to a wireless communication module (836) that facilitates wireless communication with a console (not shown) via any of a variety of wireless communication protocols such as, for example, Wi-Fi, Cellular, or Wireless Personal Area Networks (WPAN) (e.g., IrDA, Bluetooth, Bluetooth Low Energy, Zigbee, wireless USB). Surgical stapler (610) may additionally or alternatively be configured to support wired communication via a communication port (not shown), such as a USB port, for example. The console (not shown) may receive a message from wireless communication module (836) and facilitates generation of a notification to a user of the surgical stapler (610). By way of example only, the console may include a data processor and a display that cooperate to generate the notification. Further, the console may be a component of a robotic electrosurgical system. Various suitable forms that a console for surgical stapler (610) may take will be apparent to those skilled in the art in view of the teachings herein. Switch (826), microprocessor (830), and wireless communication module (836) are powered by an onboard power source (838) which can comprise a disposable battery, a rechargeable battery, a supercapacitor or any of a variety of suitable alternative power storage arrangements.

Microprocessor (830) is configured to monitor the status of switch (826) and to facilitate generation of an audible notification and/or a visual notification on the console, via wireless communication module (836), that warns the user that the tissue is improperly clamped to prevent them from firing the stapler. For example, when the tissue is improperly clamped such that switch (826) is activated, the microprocessor (830) recognizes the switch (826) as being activated and can transmit a message to the console, via wireless communication module (836), that causes the console to generate a notification that warns the user that tissue is improperly clamped to prevent them from firing provide the surgical stapler (610). The user can then reposition the stapler on tissue until proper clamping is achieved. Once the tissue is properly clamped, microprocessor (830) can stop transmitting the message to terminate the notification on the console thus indicating to the user that surgical stapling instrument (610) is ready to fire. In one example, microprocessor (830) can instead transmit a different message to the console that causes the console to display a notification to the user indicating that surgical stapler (610) is ready to fire. The notification(s) presented by the console can be a visual notification, such as message displayed on a screen or a flashing light, an audible notification, such as a chime or a recorded spoken message, or a combination thereof.

B. Clamp Force Sensor Attached to End Effector

Figure 14:
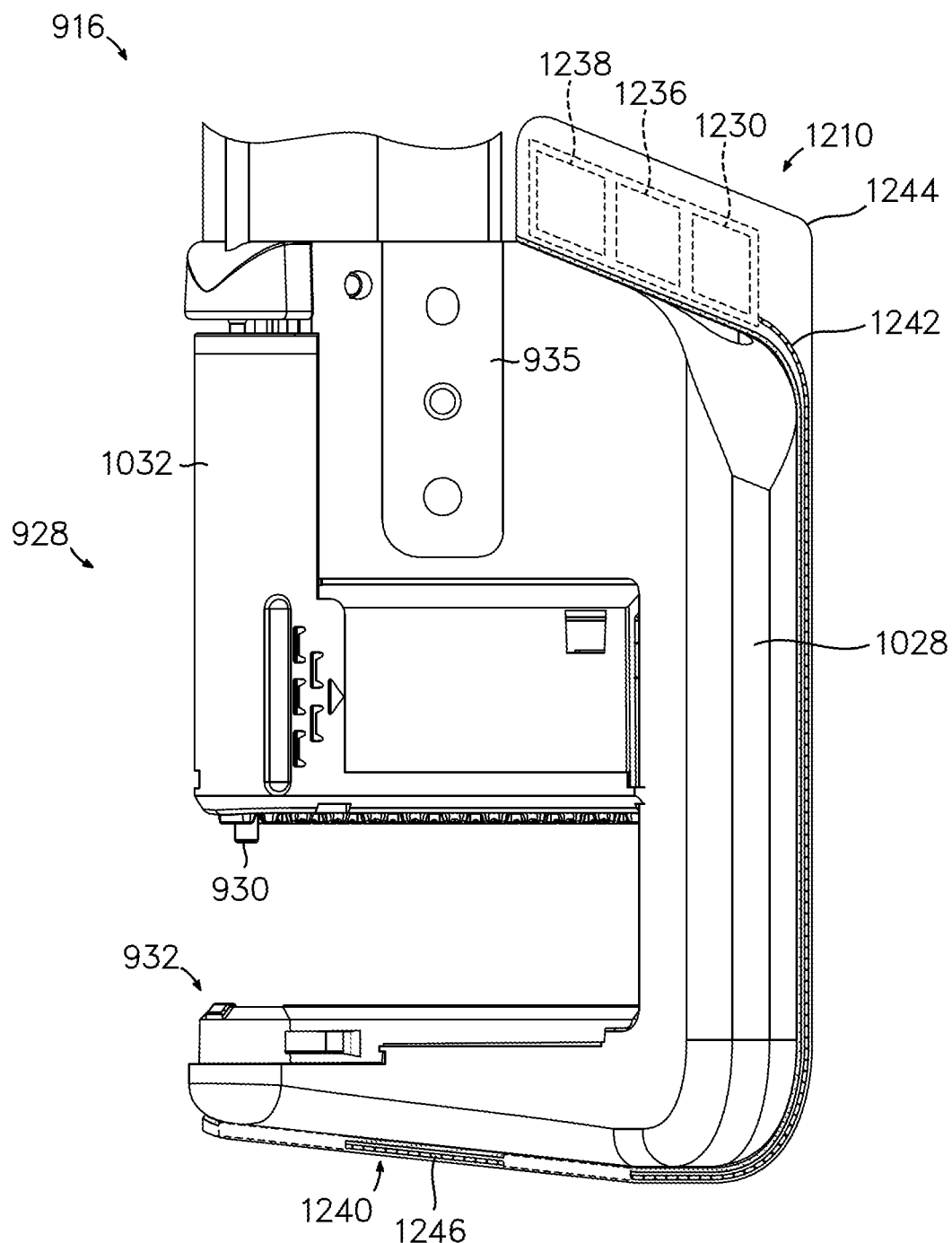
FIG. 14 depicts a left side elevational view of another illustrative end effector in association with a clamp force sensor.
Figure 15:
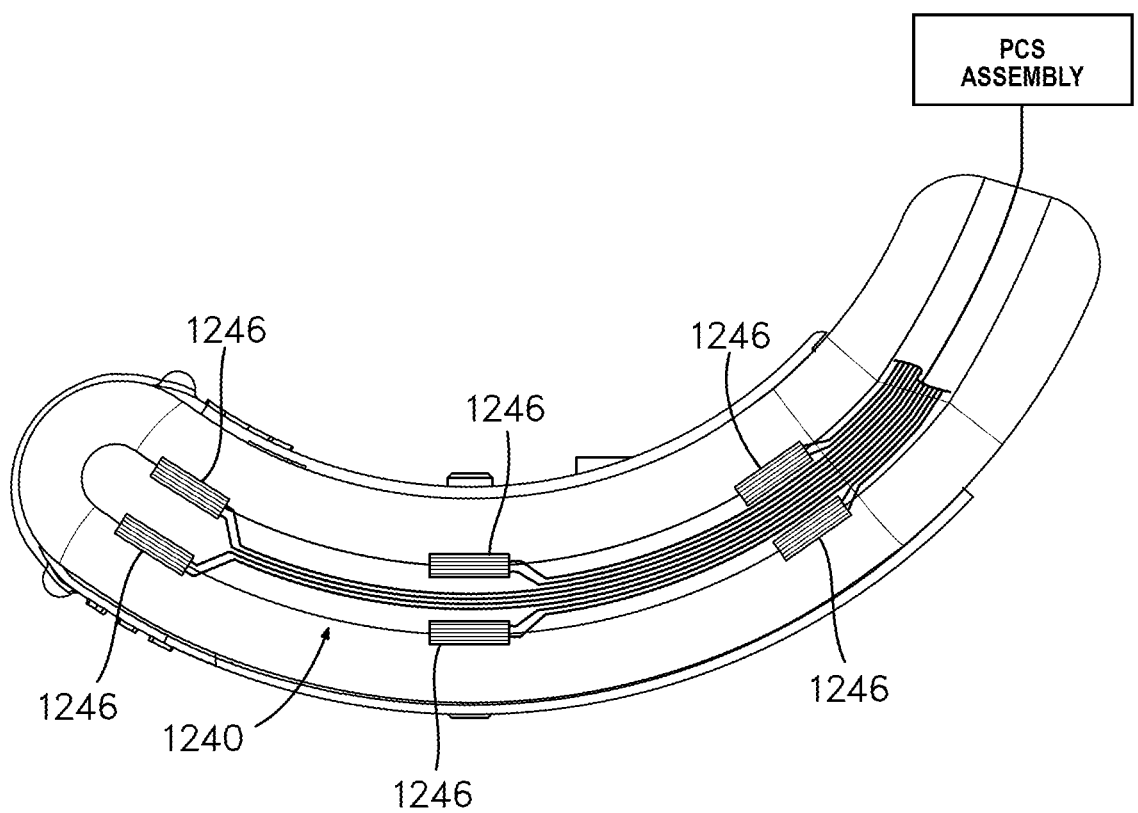
FIG. 15 depicts a bottom plan view of the end effector of FIG. 14.

FIGS. 14 and 15 show an illustrative end effector (916) that is generally similar to end effector (16) described above except as otherwise described below. End effector (916) includes a cartridge (928) and a retainer pin (930). Cartridge (928) includes an anvil (926), a plurality of staples (not shown), a knife (e.g., 32) and a cartridge housing (1032) that is slidable with respect to anvil (932) between a clamped (closed) position and an unclamped (open) position in response to actuation of a closure trigger (e.g., 20, 320, 620) to facilitate clamping of tissue at end effector (916). End effector (916) includes a supporting structure (1028) that supports cartridge (928) and is attached to handle frame plates (935).

A clamp force sensor (1210) is associated with the end effector (916) to facilitate detection of improper clamping of tissue between anvil (926) and cartridge housing (1032) as a function of deflection of the distal end of end effector (916). Clamp force sensor (1210) includes a microprocessor (1230), a wireless communication module (1236), an onboard power source (1238), and a sensing component, in the form of a strain gage (1240). Microprocessor (1230), wireless communication module (1236), and onboard power source (1238) are generally similar to microprocessor (830), wireless communication module (836), and onboard power source (838) described above except as otherwise described below. Strain gage (1240) is communicatively coupled to microprocessor (1230) via a wire (1242) and transmits deflection data to microprocessor (1230), as will be described in more detail below. Microprocessor (1230/) is communicatively coupled to wireless communication module (1236) to facilitate wireless communication with a remote console. Microprocessor (1230), wireless communication module (1236), onboard power source (1238), strain gage (1240) and wire (1242) are contained within a housing (1244) that is coupled with end effector (916). Microprocessor (1230), wireless communication module (1236), onboard power source (1238), and strain gage (1240) are arranged within housing (1244) such that microprocessor (1230), wireless communication module (1236), and onboard power source (1238), are disposed above cartridge housing (1032) and strain gage (1240) is disposed at a distal end of end effector (916) and adjacent to anvil (932).

Strain gage (1240) is configured to detect the deflection of anvil (932) that is indirectly imparted to the distal end of end effector (916). As illustrated in FIG. 15, strain gage (1240) comprises a plurality of sensing pads (1246) that are distributed along the distal end of the end effector (916) and configured to detect deflection of anvil (932) as a function of the elongation of the sensing pads (1246) when anvil (932) is flexed. It is to be appreciated that strain gage (1240) can be any other configuration that facilitates measurement of deflection and can additionally or alternatively be mounted anywhere on end effector (916).

The microprocessor (1230) is configured to detect improper clamping of the tissue as a function of the deflection of anvil (932) indirectly from deflection of the distal end of end effector (916). When tissue is clamped between anvil (932) and cartridge housing (1032) (e.g., by closing closure trigger (20, 320, 620)), the tissue may be too thick and/or improperly positioned between anvil (932) and cartridge housing (1032) to allow them to properly clamp together. Such improper clamping can cause excessive deflection of the anvil (932) and the distal end of the end effector (916). The microprocessor (1230) can therefore indirectly monitor the deflection of anvil (932) via strain gage (1240) to determine whether the tissue is improperly clamped and thus causing excessive deflection of anvil (932). If the microprocessor (1230) determines that anvil (932) is being excessively deflected by the tissue, microprocessor (1230) can transmit a message to the console, via wireless communication module (1236), that causes the console to generate a notification that warns the user that tissue is improperly clamped to prevent them from firing the stapler. The user can then reposition the stapler on the tissue until proper clamping is achieved. Once the tissue is properly clamped, microprocessor (1230) can stop transmitting the message to terminate the notification on the console thus indicating to the user that surgical stapling instrument (e.g., 10, 310, 610) is ready to fire. In one example, microprocessor (1230) can transmit a different message to the console that causes the console to display a notification to the user indicating that surgical stapling instrument is ready to fire. The notification(s) presented by the console can be a visual notification, such as message displayed on a screen or a flashing light, an audible notification, such as a chime or a recorded spoken message, or a combination thereof.

In one example, microprocessor (1230) can compare the deflection amount detected by strain gage (1240) to a threshold value to determine whether the tissue is improperly clamped. The threshold value can be understood to represent the minimum amount of deflection that the anvil (932) can undergo before cutting and/or stapling would be adversely affected. If the detected deflection is below the threshold value, thus indicating that the tissue is properly clamped, microprocessor (1230) refrains from transmitting a warning message to the console, or alternatively, transmits a permission message to the console to cause the console to notify the user that the surgical stapling instrument is ready to fire. If the detected deflection is above the threshold value, thus indicating that the tissue is improperly clamped, microprocessor (1230) transmits the warning message to the console and the console, in response, notifies the user to refrain from firing the surgical stapling instrument before releasing the tissue and reclamping.

In one configuration, strain gage (1240) and microprocessor (1230) can be selectively activated in response to clamping of the tissue in an effort to conserve power consumption. For example, prior to clamping of the tissue, such as when closure trigger (20, 320, 620) is opened, strain gage (1240) and microprocessor (1230) are deactivated (i.e., are in a sleep mode). Once the tissue is clamped between anvil (932) and cartridge housing (1032), strain gage (1240) and microprocessor (1230) can be activated to initialize sensing of the deflection of the anvil (932), as described above. The activation of strain gage (1240) and microprocessor (1230) can be a function of the position of the closure trigger. When the closure trigger is opened, strain gage (1240) and microprocessor (1230) can be deactivated. When the closure trigger is closed to clamp the tissue, the microprocessor can recognize the closing of the closure trigger and can initialize sensing of the deflection of the anvil (932) with strain gage (1240). In one example, microprocessor (1230) can recognize the status of the closure trigger via a switch (not shown) that is associated with the closure trigger and indicates whether the closure trigger is opened or closed. Anvil (932) might additionally or alternatively include a manual switch, such as a pushbutton or a microswitch that allows a user to manually control the activation of strain gage (1240) and microprocessor (1230) through activation of the switch.

The clamp force sensor (1210) is intended to be provided as a standalone device that can be incorporated onto a conventional end effector (e.g., 16) in order to add the sensing functionality described above to a surgical stapler instrument (e.g., 10). In some instances, clamp force sensor (1210) can be provided as an aftermarket solution for adding the sensing functionality described above to an existing surgical stapling instrument, such as a surgical stapling instrument that has already been placed in service. As such, clamp force sensor (1210) provides a cost effective and simple solution for providing the sensing functionality described above to a surgical stapling instrument that may not otherwise have such functionality.

Figure 16C:
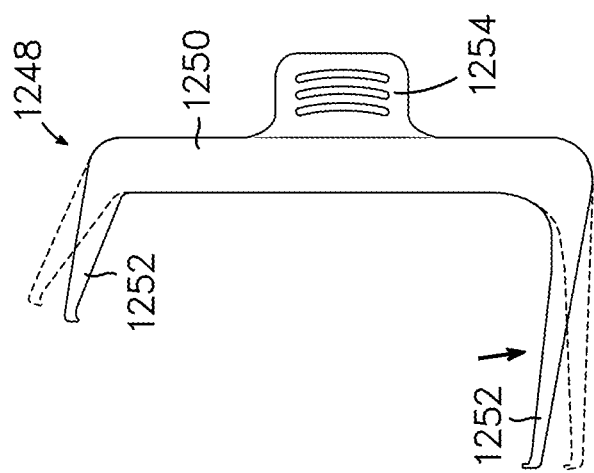
FIG. 16C depicts a right side elevational view of an applicator that is removed from the clamp force sensor of FIGS. 14 and 15.
Figure 16B:
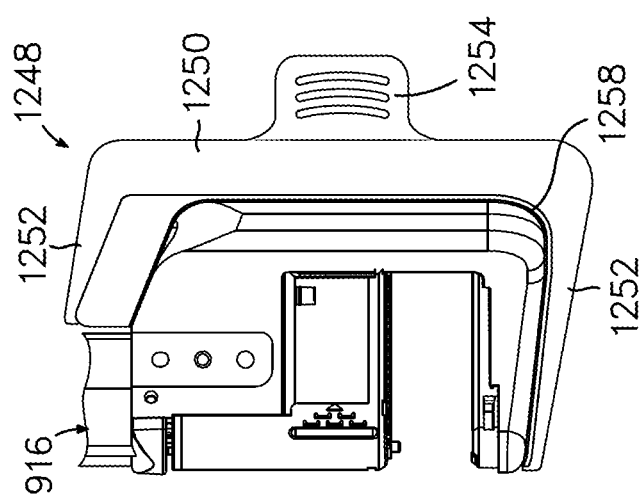
FIG. 16B depicts the applicator of FIG. 16A in association with the clamp force sensor of FIGS. 14 and 15.
Figure 16A:
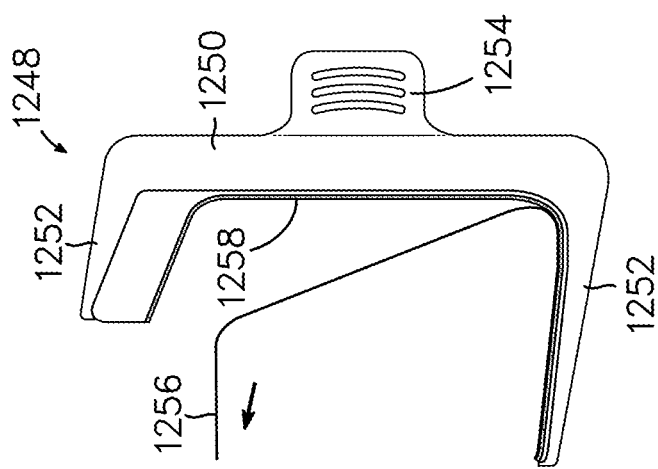
FIG. 16A depicts a right side elevational view of an applicator for use with the clamp force sensor of FIGS. 14 and 15.

To that end, FIGS. 16A-16C illustrate an applicator (1248) that can be provided as an accessory for clamp force sensor (1210) that facilitates installation of clamp force sensor (1210) onto end effector (916). As illustrated in FIG. 16A, applicator (1248) includes a central body (1250) and a pair of grasping features (1252) that extend from central body (1250) and are spaced from each other. A tab (1254) extends laterally from central body (1250). Central body (1250) and grasping features (1252) have an overall internal profile that generally conforms to an outer profile of housing (1244).

The method of installing clamp force sensor (1210) using applicator (1248) will now be described with reference to FIGS. 16A-16C. First, clamp force sensor (1210) can be pressed into applicator (1248) such that grasping features (1252) initially spread apart to accept clamp force sensor (1210) and then are clamped over clamp force sensor (1210) to hold it in place once it is fully installed on applicator (1248), as illustrated in FIG. 16A. A protective layer (1256) is then removed from an adhesive strip (1258) that is routed along and adhered to an interior surface of clamp force sensor (1210) to expose an adhesive outer surface of adhesive strip (1258). With protective layer (1256) removed, a user can push clamp force sensor (1210) into place over end effector (916) with enough force to properly adhere adhesive strip (1258) to end effector (916), as illustrated in FIG. 16B. With clamp force sensor (1210) adhered to end effector (916), applicator (1248) can then be removed from clamp force sensor (1210) by pulling grasp tab (1254) with enough force to cause grasping features (1252) to spread apart and disengage from clamp force sensor (1210).

C. Clamp Force Sensor Incorporated into Cartridge

Figure 17:
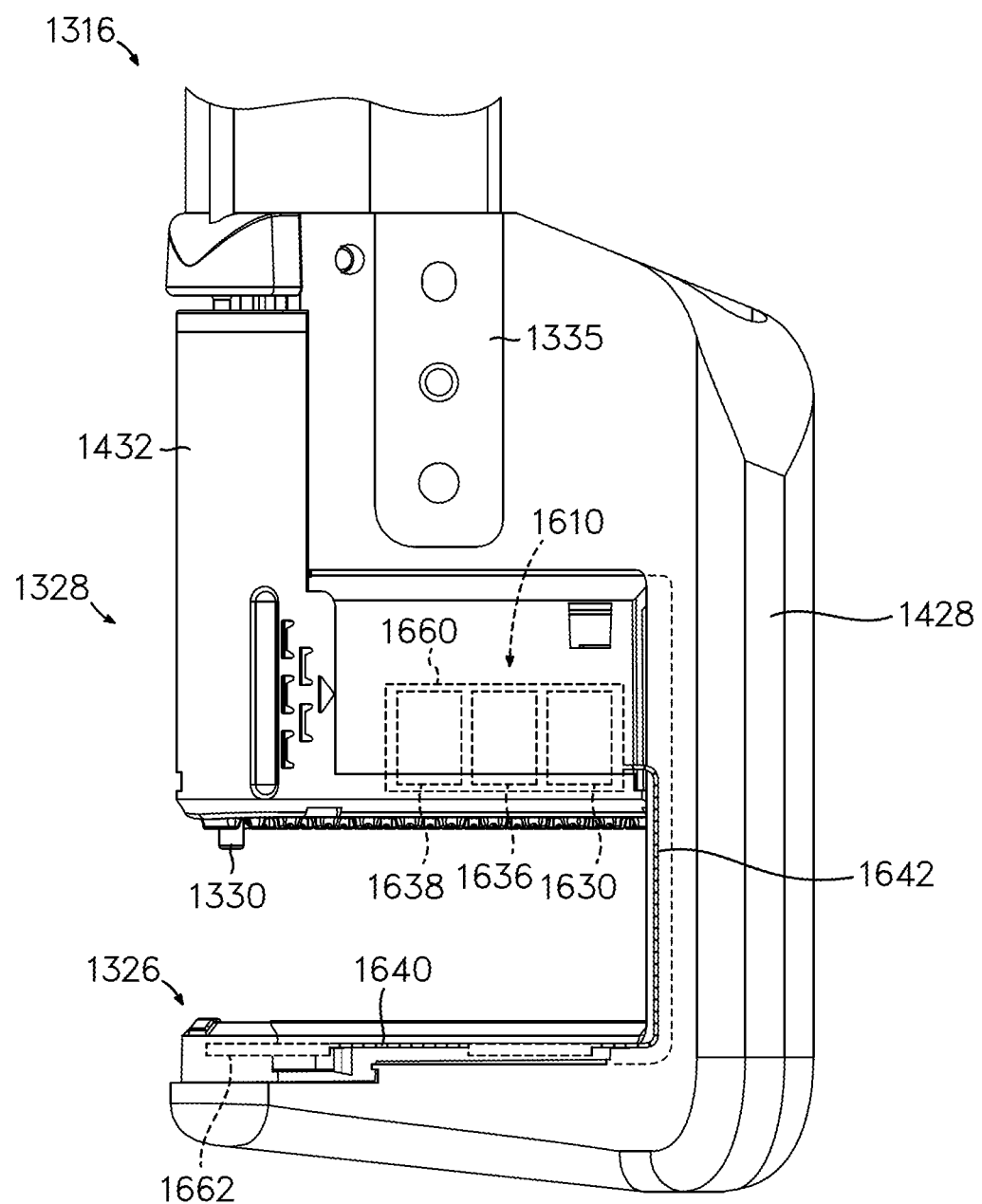
FIG. 17 depicts a left side elevational view of another illustrative end effector that includes a staple cartridge having a clamp force sensor housed therein.

FIG. 17 shows an illustrative end effector (1316) that is generally similar to end effector (916) described above except as otherwise described below. End effector (1316) includes a cartridge (1328) and a retainer pin (1330). Cartridge (1328) includes an anvil (1326), a plurality of staples (not shown), a knife (e.g., 32) and a cartridge housing (1432) that is slidable with respect to anvil (1326) between a clamped (closed) position and an unclamped (open) position in response to actuation of a closure trigger (e.g., 20, 320, 620) to facilitate clamping of tissue at end effector (1316). End effector (1316) includes a supporting structure (1428) that supports cartridge (1328) and is attached to handle frame plates (1335).

A clamp force sensor (1610) is incorporated into cartridge (1328) to facilitate detection of improper clamping of tissue between anvil (1326) and cartridge housing (1432). The clamp force sensor (1610) includes a microprocessor (1630), a wireless communication module (1636), an onboard power source (1638), and a sensing component, in the form of a strain gage (1640). Strain gage (1640) is communicatively coupled to microprocessor (1630) via a wire (1642). Microprocessor (1630) is communicatively coupled to wireless communication module (1636) to facilitate wireless communication with a remote console. Microprocessor (1630), wireless communication module (1636), and onboard power source (1638) are disposed within an interior chamber (1660) that is defined by cartridge housing (1432) such that microprocessor (1630), wireless communication module (1636), and onboard power source (1638) are disposed above cartridge housing (1432).

Strain gage (1640) is configured to detect the deflection of anvil (1326) that occurs as a result of clamping tissue between anvil (1326) and cartridge housing (1432). As illustrated in FIG. 17, strain gage (1640) is disposed within an interior chamber (1662) that is defined by anvil (1326) and extends along the anvil (1326) to facilitate detection of the deflection of anvil (1326) directly from anvil (1326). The microprocessor (1630) is configured to detect improper clamping of the tissue as a function of the deflection of anvil (1326) and facilitate generate of a notification on a remote console when the tissue is improperly clamped to prevent a user from firing the surgical stapler instrument.

By integrating clamp force sensor (1610) into cartridge (1328), cartridge (1328) can be provided as a standalone device that can be incorporated onto a conventional end effector (e.g., 16) in order to add the sensing functionality described above to a surgical stapler instrument (e.g., 10). In some instances, cartridge (1328) can be provided as an aftermarket solution for adding the sensing functionality described above to an existing surgical stapling instrument, such as a surgical stapling instrument that has already been placed in service. As such, cartridge (1328) provides a cost effective and simple solution for providing the sensing functionality described above to a surgical stapling instrument that may not otherwise have such functionality.

D. Clamp Force Sensor Incorporated into End Effector

Figure 18:
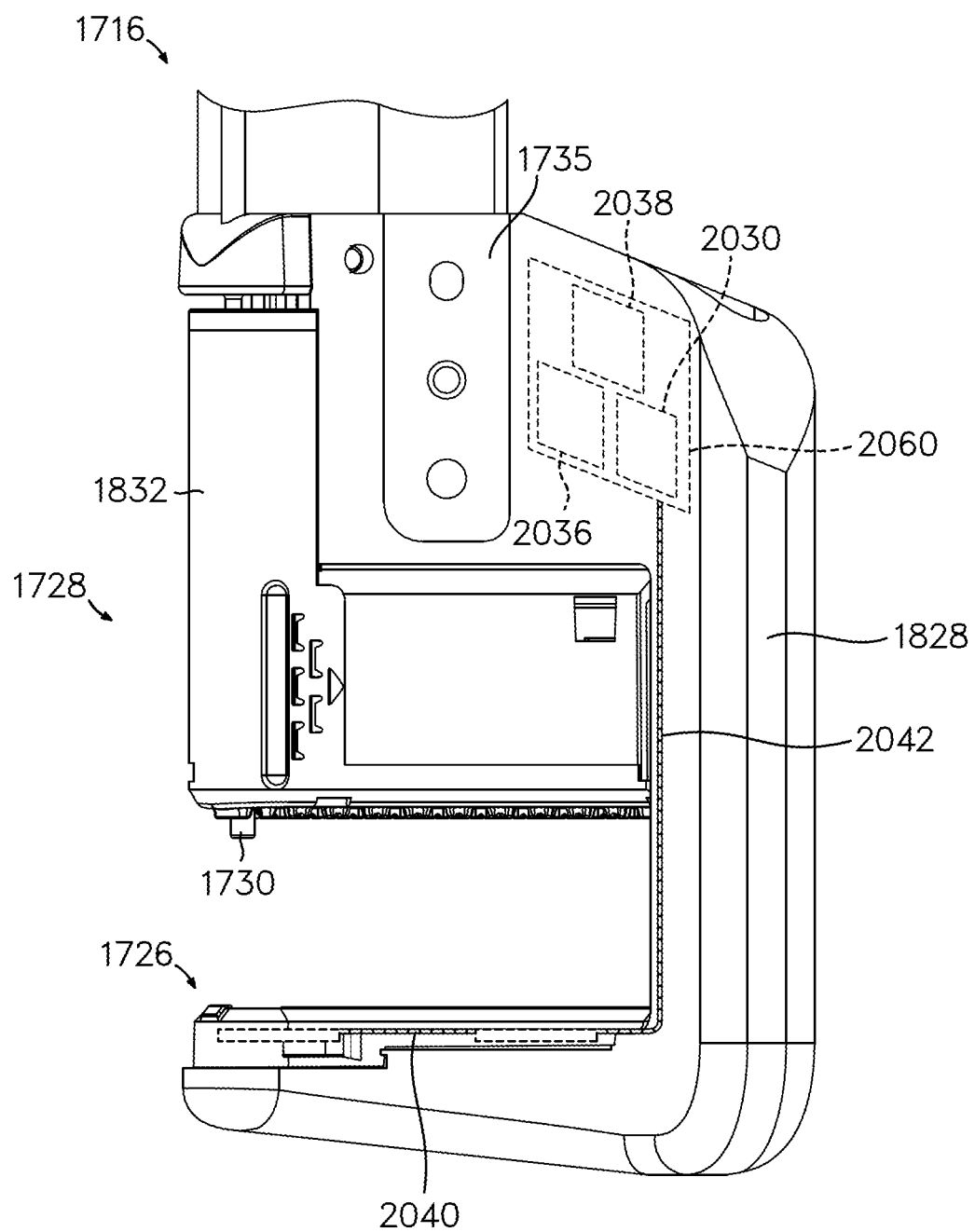
FIG. 18 depicts a left side elevational view of another illustrative end effector that includes clamp force sensor housed therein.

FIG. 18 shows an illustrative end effector (1716) that is generally similar to end effector (916) described above except as otherwise described below. End effector (1716) includes a cartridge (1728) and a retainer pin (1730). Cartridge (1728) includes an anvil (1726), a plurality of staples (not shown), a knife (e.g., 32) and a cartridge housing (1832) that is slidable with respect to anvil (1726) between a clamped (closed) position and an unclamped (open) position in response to actuation of a closure trigger (e.g., 20, 320, 620) to facilitate clamping of tissue at end effector (1716). End effector (1716) includes a supporting structure (1828) that supports cartridge (1728) and is attached to handle frame plates (1735).

A clamp force sensor is incorporated into supporting structure (1828) of end effector (1716) to facilitate detection of improper clamping of tissue between anvil (1726) and cartridge housing (1832). The clamp force sensor includes a microprocessor (2030), a wireless communication module (2036), an onboard power source (2038), and a sensing component, in the form of a strain gage (2040). Strain gage (2040) is communicatively coupled to microprocessor (2030) via a wire (2042). Microprocessor (2030) is communicatively coupled to wireless communication module (2036) to facilitate wireless communication with a remote console. Microprocessor (2030), wireless communication module (2036), and onboard power source (2038) are disposed within an interior chamber (2060) that is defined by supporting structure (1828) such that microprocessor (2030), wireless communication module (2036), and onboard power source (2038) are disposed above cartridge housing (1832).

Strain gage (2040) is configured to detect the deflection that occurs at the interface between anvil (1726) and the distal end of supporting structure (1828) as a result of clamping tissue between anvil (1326) and cartridge housing (1432). As illustrated in FIG. 17, strain gage (2040) is provided at the interface between anvil (1726) and the extends along the anvil (1726) to facilitate detection of the deflection of anvil (1326) from beneath the anvil (1726). The microprocessor (2030) is configured to detect improper clamping of the tissue as a function of deflection beneath anvil (1726) and facilitate generate of a notification on a remote console when the tissue is improperly clamped to prevent a user from firing the surgical stapler instrument.

E. Clamp Force Sensor Incorporated into Firing Bar

Figure 19:
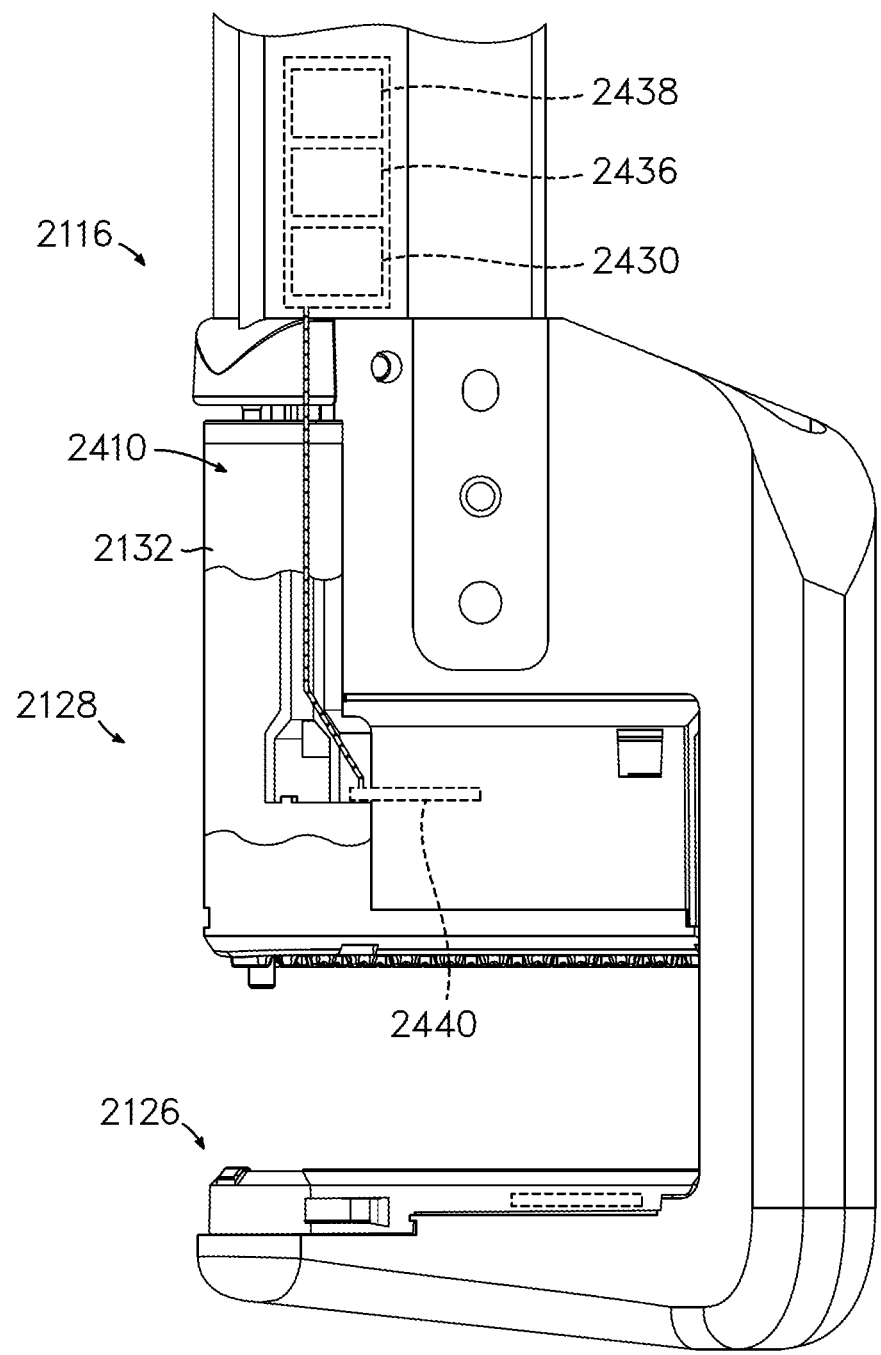
FIG. 19 depicts a left side elevational view of another illustrative end effector that includes a clamp force sensor having a sensing component disposed between a firing bar and a knife.

FIG. 19 shows an illustrative end effector (2116) that is generally similar to end effector (916) described above except as otherwise described below. End effector (2116) includes a cartridge (2128) that includes an anvil (2126), a plurality of staples (not shown), a knife (e.g., 32) and a cartridge housing (2132) that is slidable with respect to anvil (2126) between a clamped (closed) position and an unclamped (open) position in response to actuation of a closure trigger (e.g., 20, 320, 620) to facilitate clamping of tissue at end effector (2116). End effector (2116) further includes a firing bar (e.g., 82) that interacts with cartridge (2128) to facilitate formation of staples (not shown) in the tissue and/or severing of the tissue with knife (e.g., 32).

A clamp force sensor (2410) is incorporated into cartridge (2128) to facilitate detection of improper clamping of tissue between anvil (1326) and cartridge housing (1432). The clamp force sensor (2410) includes a microprocessor (2430), a wireless communication module (2436), an onboard power source (2438), and a sensing component, in the form of a strain gage (2440). Strain gage (2440) is incorporated between the firing bar and the knife and is configured to facilitate detection of the distance and clamping force between anvil (2126) and cartridge housing (2132) during firing of the surgical stapling instrument.

F. Clamp Force Sensor Incorporated into Cuff Attached to Support Structure

Figure 20:
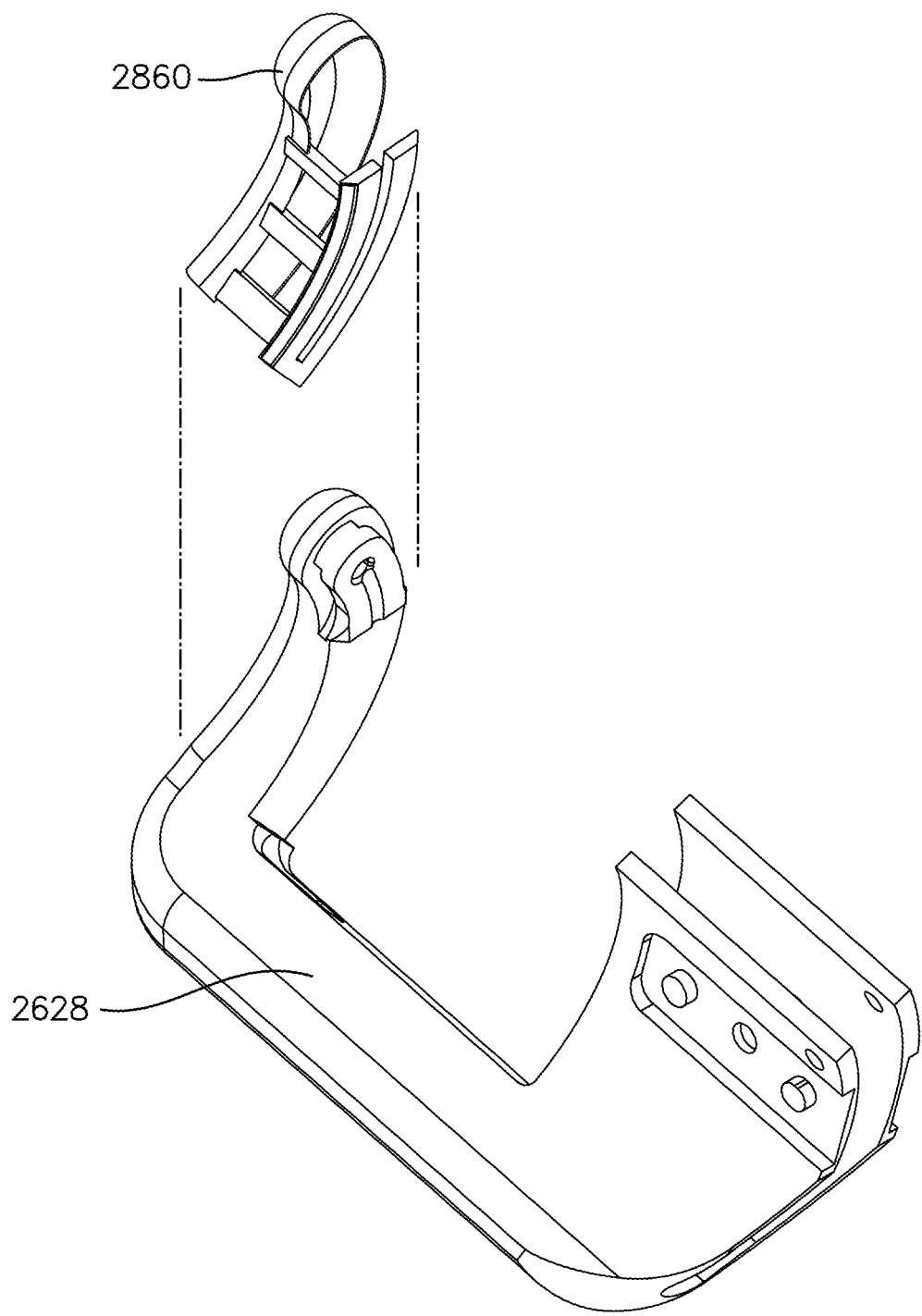
FIG. 20 depicts an exploded perspective view of another illustrative end effector and an intelligent cuff.
Figure 21:
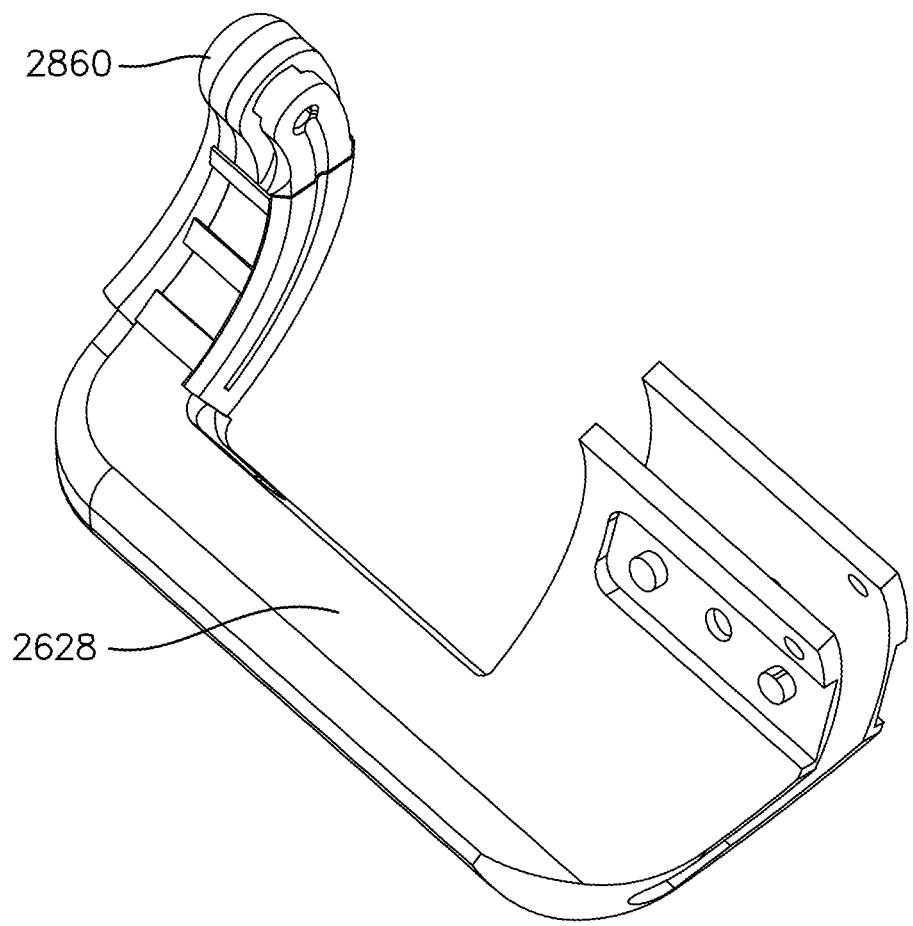
FIG. 21 depicts a perspective view of the intelligent cuff of FIG. 20 installed on the end effector.
Figure 22:
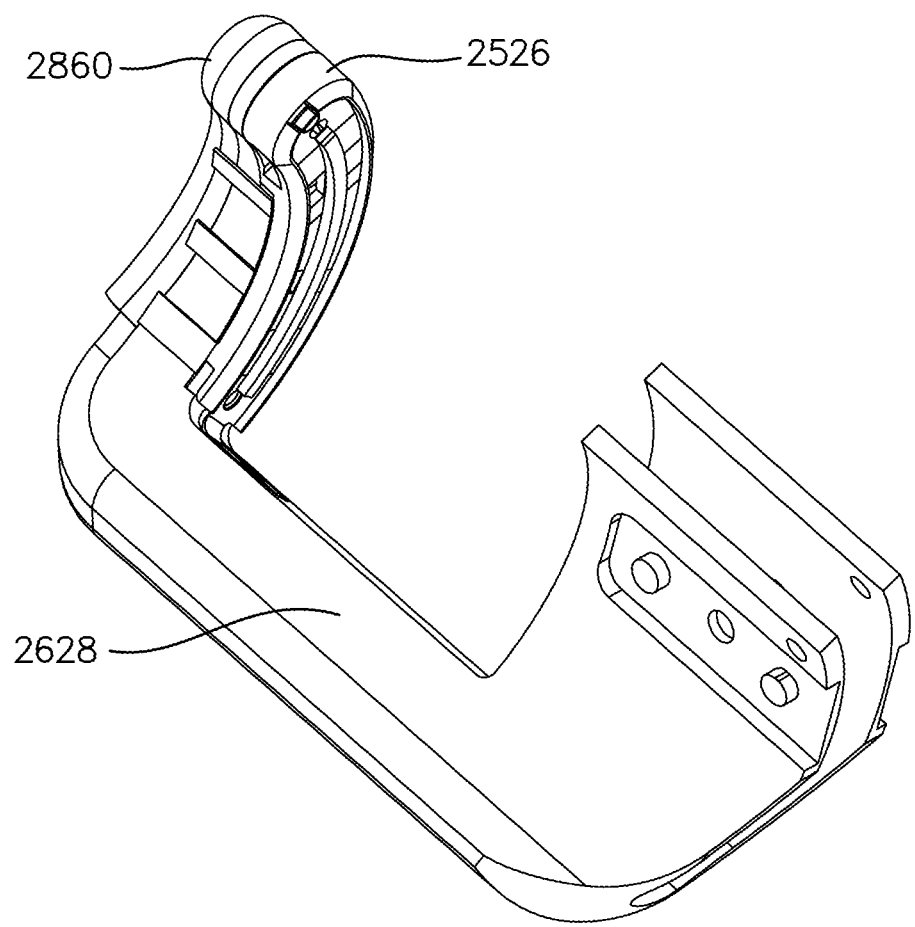
FIG. 22 depicts a perspective view of an anvil installed on the intelligent cuff of FIG. 21.

FIGS. 20-22 shows an illustrative supporting structure (2628) for an end effector (e.g., 16, 616, 916) that is generally similar to supporting structures (128, 1028, 1428) described above except as otherwise described below. Supporting structure (2628) includes an intelligent cuff (2860) that is configured for installation over a distal end of supporting structure (2628), as illustrated in FIGS. 20 and 21. Cuff (2860) includes a strain gage (not shown) that facilitates detection of a clamping force at the distal end of supporting structure (2628). Cuff (2860) is communicatively coupled with a microprocessor (not shown) and a wireless communication module (not shown) that cooperate to provide clamping force feedback to a user in a similar manner as described above. As illustrated in FIG. 22, an anvil (2526) is attached to cuff (2860) to facilitate the formation of staples thereon.

III. Illustrative Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus, comprises (a) a handle assembly comprising a closure trigger that is pivotable between a released position and an actuated position; (b) a shaft assembly; (c) an end effector coupled with the shaft assembly and comprising a cartridge that includes an anvil and a cartridge housing, the cartridge housing being slidable with respect to the anvil between an unclamped position and a clamped position to facilitate selective clamping of patient tissue therebetween; and (d) a clamp force sensor associated with the end effector and configured to detect a clamping force between the anvil and the cartridge housing and facilitate generation of a notification as a function of the detected clamping force.

Example 2

The apparatus of Example 1, wherein the clamp force sensor comprises a sensing component, a controller in signal communication with the sensing component, a communication module that facilitates communication with a remote computing device, and a power module that facilitates powering of the clamp force sensor.

Example 3

The apparatus of Example 2, wherein: (a) the end effector further comprises a supporting structure configured to facilitate selective retention of the cartridge, (b) the clamp force sensor is coupled with the supporting structure such that the sensing component is located at a distal end of the end effector adjacent to the anvil, and (c) the controller, the communication module, and the power module are located at a proximal end of the end effector adjacent the cartridge housing.

Example 4

The apparatus of Example 3, wherein the sensing component, the controller, the communication module, and the power module are disposed within a housing that is releasably coupled to the supporting structure.

Example 5

The apparatus of Example 4, wherein the housing is releasably coupled to the supporting structure with adhesive.

Example 6

The apparatus of Example 5, in combination with an applicator that is configured for releasably grasping the housing to facilitate selective installation of the housing onto the support structure.

Example 7

The apparatus of any of Examples 6 and 7, wherein the sensing component comprises a strain gage, the power module comprises a battery, and the communication module comprises a wireless communication module that facilitates wireless communication with the remote computing device.

Example 8

The apparatus of any of Examples 4-7, wherein the supporting structure defines an interior chamber and the sensing component, the controller, the communication module, and the power module are disposed within the interior chamber.

Example 9

The apparatus of Example 8, wherein (i) the sensing component is located at a distal end of the end effector adjacent to the anvil and the controller, (ii) the communication module, and the power module are located at a proximal end of the end effector adjacent the cartridge housing, and (iii) the sensing component is coupled with communication module with a wire that extends therebetween and is disposed in the interior chamber.

Example 10

The apparatus of any of Examples 8 and 9, wherein the sensing component comprises a strain gage, the power module comprises a battery, and the communication module comprises a wireless communication module that facilitates wireless communication with the remote computing device.

Example 11

The apparatus of any of Examples 2-10, wherein the sensing component, the controller, the communication module, and the power module are coupled with the cartridge.

Example 12

The apparatus of Example 11, wherein (i) the cartridge housing defines a first interior chamber, and (ii) the controller, the communication module, and the power module are disposed within the first interior chamber.

Example 13

The apparatus of Example 12, wherein the sensing component is coupled with the anvil.

Example 14

The apparatus of Example 13, wherein (i) the anvil defines a second interior chamber, (ii) the sensing component is disposed within the first interior chamber, and (iii) the sensing component is coupled with communication module with a wire that extends between the first interior chamber and the second interior chamber.

Example 15

The apparatus of any of Examples 11-14, wherein the sensing component comprises a strain gage, the power module comprises a battery, and the communication module comprises a wireless communication module that facilitates wireless communication with the remote computing device.

Example 16

An apparatus, comprises (a) a handle assembly comprising a closure trigger that is pivotable between a released position and an actuated position; (b) a shaft assembly; (c) an end effector coupled with the shaft assembly and comprising an anvil and a cartridge housing, the cartridge housing being slidable with respect to the anvil between an unclamped position and a clamped position to facilitate selective clamping of patient tissue therebetween and (d) a clamp force sensing link operably coupled with the shaft assembly and the closure trigger such that pivoting of the closure trigger from the released position to the actuated position facilitates actuation of the end effector from the unclamped position to the clamped position via the clamp force sensing link and the shaft assembly, wherein the clamp force sensing link is configured to detect a force exerted by the closure trigger on the end effector to facilitate generation of a notification as a function of the detected force.

Example 17

The apparatus of Example 16, wherein the clamp force sensing link is configured to facilitate generation of an alarm when the detected force exceeds a threshold value.

Example 18

The apparatus of Example 17, wherein the clamp force sensing link comprises: (i) a rod and a sleeve coupled with opposing ones of the closure trigger and the shaft assembly; (ii) a spring that biases the rod and sleeve apart; and (iii) a switch assembly that is selectively activated when the rod and the sleeve are compressed together beyond a predefined distance.

Example 19

The apparatus of any of Examples 16-18, wherein the notification comprises one of a visual alarm or an audible alarm.

Example 20

A cartridge for a surgical stapler, the cartridge comprises (a) an anvil; (b) a cartridge housing that is slidable with respect to the anvil between an unclamped position and a clamped position to facilitate selective clamping of patient tissue between the anvil and the cartridge housing; and (c) a clamp force sensor comprising a sensing component, a controller in signal communication with the sensing component, a communication module that facilitates communication with a remote computing device, and a power module that facilitates powering of the clamp force sensor, wherein the clamp force sensor is configured to detect a clamping force between the anvil and the cartridge housing and facilitate generation of a notification as a function of the detected clamping force.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The surgical instrument systems described herein have been described in connection with the deployment and deformation of staples; however, the embodiments described herein are not so limited. Various embodiments are envisioned which deploy fasteners other than staples, such as clamps or tacks, for example. Moreover, various embodiments are envisioned which utilize any suitable means for sealing tissue. For instance, an end effector in accordance with various embodiments can comprise electrodes configured to heat and seal the tissue. Also, for instance, an end effector in accordance with certain embodiments can apply vibrational energy to seal the tissue.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, comprising:
   (a) a handle assembly comprising a closure trigger that is pivotable between a released position and an actuated position;
   (b) a shaft assembly;
   (c) an end effector coupled with the shaft assembly and comprising a cartridge that includes an anvil and a cartridge housing, the cartridge housing being slidable with respect to the anvil between an unclamped position and a clamped position to facilitate selective clamping of patient tissue therebetween; and
   (d) a sensor fixed relative to the anvil and configured to detect deflection of the anvil relative to the cartridge housing in the clamped position and facilitate generation of a notification as a function of the detected deflection.

2. The apparatus of claim 1, wherein the sensor comprises a sensing component, a controller in signal communication with the sensing component, a communication module that facilitates communication with a remote computing device, and a power module that facilitates powering of the sensor.

3. The apparatus of claim 2, wherein:
   (a) the end effector further comprises a supporting structure configured to facilitate selective retention of the cartridge,
   (b) the sensor is coupled with the supporting structure such that the sensing component is located at a distal end of the end effector, and
   (c) the controller, the communication module, and the power module are located at a proximal end of the end effector.

4. The apparatus of claim 3, wherein the sensing component, the controller, the communication module, and the power module are disposed within a housing that is releasably coupled to the supporting structure.

5. The apparatus of claim 4, wherein the housing is releasably coupled to the supporting structure with adhesive.

6. The apparatus of claim 5 in combination with an applicator that is configured for releasably grasping the housing to facilitate selective installation of the housing onto the support structure.

7. The apparatus of claim 5, wherein the sensing component comprises a strain gage, the power module comprises a battery, and the communication module comprises a wireless communication module that facilitates wireless communication with the remote computing device.

8. The apparatus of claim 3, wherein the supporting structure defines an interior chamber and the sensing component, the controller, the communication module, and the power module are disposed within the interior chamber.

9. The apparatus of claim 8, wherein the sensing component is coupled with the communication module with a wire that extends therebetween and is disposed in the interior chamber.

10. The apparatus of claim 8, wherein the sensing component comprises a strain gage, the power module comprises a battery, and the communication module comprises a wireless communication module that facilitates wireless communication with the remote computing device.

11. The apparatus of claim 2, wherein the sensing component, the controller, the communication module, and the power module are coupled with the cartridge.

12. The apparatus of claim 11, wherein:
   (i) the cartridge housing defines a first interior chamber, and
   (ii) the controller, the communication module, and the power module are disposed within the first interior chamber.

13. The apparatus of claim 12, wherein the sensing component is coupled with the anvil.

14. The apparatus of claim 13, wherein:
   (i) the anvil defines a second interior chamber,
   (ii) the sensing component is disposed within the first interior chamber, and
   (iii) the sensing component is coupled with communication module with a wire that extends between the first interior chamber and the second interior chamber.

15. The apparatus of claim 11, wherein the sensing component comprises a strain gage, the power module comprises a battery, and the communication module comprises a wireless communication module that facilitates wireless communication with the remote computing device.

16. An apparatus, comprising:
   (a) a handle assembly comprising a closure trigger that is pivotable between a released position and an actuated position;
   (b) a shaft assembly;
   (c) an end effector coupled with the shaft assembly and comprising an anvil and a cartridge housing, the cartridge housing being slidable with respect to the anvil between an unclamped position and a clamped position to facilitate selective clamping of patient tissue therebetween; and
   (d) a clamp force sensing link operably coupled with the shaft assembly and the closure trigger such that pivoting of the closure trigger from the released position to the actuated position facilitates actuation of the end effector from the unclamped position to the clamped position via the clamp force sensing link and the shaft assembly, wherein the clamp force sensing link is configured to detect a force exerted by the closure trigger on the end effector to facilitate generation of a notification as a function of the detected force.

17. The apparatus of claim 16, wherein the clamp force sensing link is configured to facilitate generation of an alarm when the detected force exceeds a threshold value.

18. The apparatus of claim 17, wherein the clamp force sensing link comprises:
   (i) a rod and a sleeve coupled with the closure trigger and the shaft assembly;

(ii) a spring that biases the rod and sleeve apart; and
(iii) a switch assembly that is selectively activated when the rod and the sleeve are compressed together beyond a predefined distance.

19. The apparatus of claim 16, wherein the notification comprises one of a visual alarm or an audible alarm.

20. A surgical stapler end effector comprising:
(a) an anvil;
(b) a cartridge housing that is slidable with respect to the anvil between an unclamped position and a clamped position to facilitate selective clamping of patient tissue between the anvil and the cartridge housing; and
(c) a sensor comprising a sensing component fixed relative to the anvil, a controller in signal communication with the sensing component, a communication module that facilitates communication with a remote computing device, and a power module that facilitates powering of the sensor, wherein the sensor is configured to detect deflection of the anvil and facilitate generation of a notification as a function of the detected deflection.

\* \* \* \* \*